US012336971B2

(12) United States Patent
Joshi

(10) Patent No.: US 12,336,971 B2
(45) Date of Patent: *Jun. 24, 2025

(54) OPHTHALMIC PHARMACEUTICAL COMPOSITIONS AND USES THEREOF

(71) Applicant: ALCON INC., Fribourg (CH)

(72) Inventor: Anjali Joshi, Durham, NC (US)

(73) Assignee: Alcon Inc., Fribourg (CH)

( * ) Notice: Subject to any disclaimer, the term of this patent is extended or adjusted under 35 U.S.C. 154(b) by 0 days.

This patent is subject to a terminal disclaimer.

(21) Appl. No.: 18/510,437

(22) Filed: Nov. 15, 2023

(65) Prior Publication Data

US 2024/0091179 A1 Mar. 21, 2024

Related U.S. Application Data

(63) Continuation of application No. 18/082,844, filed on Dec. 16, 2022, now Pat. No. 11,850,221.

(60) Provisional application No. 63/290,781, filed on Dec. 17, 2021.

(51) Int. Cl.
| | |
|---|---|
| *A61K 31/167* | (2006.01) |
| *A61K 9/00* | (2006.01) |
| *A61K 47/02* | (2006.01) |
| *A61K 47/38* | (2006.01) |
| *A61K 47/44* | (2017.01) |
| *A61P 27/04* | (2006.01) |

(52) U.S. Cl.
CPC .......... *A61K 31/167* (2013.01); *A61K 9/0048* (2013.01); *A61K 47/02* (2013.01); *A61K 47/38* (2013.01); *A61K 47/44* (2013.01); *A61P 27/04* (2018.01)

(58) Field of Classification Search
CPC .... A61K 31/167; A61K 9/0046; A61K 47/38; A61P 47/38
See application file for complete search history.

(56) References Cited

U.S. PATENT DOCUMENTS

| | | |
|---|---|---|
| 6,919,348 B2 | 7/2005 | Wei |
| 7,893,110 B2 | 2/2011 | Galopin et al. |
| 9,095,609 B2 | 8/2015 | Martinez et al. |
| 9,433,679 B2 | 9/2016 | Martinez et al. |
| 9,901,549 B2 | 2/2018 | Martinez et al. |
| 10,028,920 B2 | 7/2018 | Martinez et al. |
| 11,850,221 B2 | 12/2023 | Joshi |
| 2002/0009507 A1 | 1/2002 | Weimer et al. |
| 2003/0008805 A1 | 1/2003 | Honma et al. |
| 2005/0090514 A1 | 4/2005 | Reynolds et al. |
| 2005/0137166 A1 | 6/2005 | Asgharian et al. |
| 2006/0111388 A1 | 5/2006 | Dibas et al. |
| 2007/0010574 A1 | 1/2007 | Plath et al. |
| 2008/0214654 A1 | 9/2008 | Lampe et al. |
| 2008/0253973 A1 | 10/2008 | Tamarkin et al. |
| 2009/0269369 A1 | 10/2009 | Doi et al. |
| 2010/0048619 A1 | 2/2010 | Colburn et al. |
| 2011/0053137 A1 | 3/2011 | Julius et al. |
| 2011/0223222 A1 | 9/2011 | Spyros Botsaris et al. |
| 2013/0245231 A1 | 9/2013 | Martinez et al. |
| 2015/0290151 A1 | 10/2015 | Birbara et al. |
| 2018/0333414 A1 | 11/2018 | Musunuri et al. |
| 2020/0306218 A1 | 10/2020 | Galan Valdivia |
| 2022/0080048 A1 | 3/2022 | Horn |

FOREIGN PATENT DOCUMENTS

| | | |
|---|---|---|
| EP | 3406600 A1 | 11/2018 |
| EP | 3705114 A1 | 9/2020 |
| GB | 2451503 A | 2/2009 |
| JP | H1067684 A | 3/1998 |
| JP | H10236972 A | 9/1998 |
| JP | 2001-122774 A | 5/2001 |
| JP | 2006193521 A | 7/2006 |
| WO | 2001/041806 A1 | 6/2001 |
| WO | 2003/099278 A1 | 12/2003 |
| WO | 2007/017092 A1 | 2/2007 |
| WO | 2007/099503 A2 | 9/2007 |
| WO | 2008/066644 A1 | 6/2008 |
| WO | 2010/017609 A2 | 2/2010 |
| WO | 2010/021882 A2 | 2/2010 |
| WO | 2012/032209 A2 | 3/2012 |
| WO | 2018/067895 A1 | 4/2018 |
| WO | 2020/178429 A1 | 9/2020 |
| WO | 2021/195256 A1 | 9/2021 |
| WO | 2023/114986 A1 | 6/2023 |

OTHER PUBLICATIONS

Extended European Search Report dated Sep. 26, 2019 for European Application Serial No. 19382170.9.

Jiao et al., "Polyoxyethylated nonionic surfactants and their applications in topical ocular drug delivery", Advanced Drug delivery reviews, Elsevier, vol. 60, No. 15, Dec. 14, 2008 (Dec. 14, 2008), pp. 1663-1673.

Sahoo et al., "Nonionic Surfactant Vesicles in Ocular Delivery: Innovative Approaches and Perspectives", Biomed Research International, vol. 2014, Jan. 1, 2014 (Jan. 1, 2014), pp. 1-12.

International Search Report and Written Opinion, mailed Apr. 24, 2020, for International Application Serial No. PCT/EP2020/056023 filed Mar. 6, 2020.

Fawzia et al., "Ocular drug deliver and the importance of microemulsion as a potential delivery system", International Journal of Pharmaceutical and Chemical Sciences, vol. 1 (2) Apr.-Jun. 2012, pp. 723-737.

Chen et al., "Borneol Is a TRPM8 Agonist that Increases Ocular Surface Wetness", Plos One, vol. 11, No. 7, pp. 1-15, Year: 2016).

(Continued)

*Primary Examiner* — Sikarl A Witherspoon
(74) *Attorney, Agent, or Firm* — K&L Gates LLP; Louis C. Cullman; Benjamin D. Heuberger

(57) ABSTRACT

Provided herein are ophthalmic pharmaceutical compositions comprising (1R,2S,5R)-2-isopropyl-N-(4-methoxyphenyl)-5-methylcyclohexane-1-carboxamide (WS-12) for effectively treating dry eye in a subject in need thereof, effectively reducing dry eye in a subject in need thereof, effectively reducing the likelihood of dry eye in a subject in need thereof, or for treating, preventing, or ameliorating signs or symptoms of dry eye in a subject in need thereof.

4 Claims, 8 Drawing Sheets

(56) References Cited

OTHER PUBLICATIONS

International Search Report and Written Opinion, mailed Mar. 21, 2012, for International Application Serial No. PCT/ES2011/070627 filed Sep. 8, 2011.
Haghighi et al., "Therapeutic potentials of menthol in migraine headache: Possible mechanisms of action", Medical hipothesis, 2007, vol. 69,(2), p. 455.
Parra et al., "Ocular surface wetness is regulated by TRPM8-dependent cold thermoreceptors of the cornea", Nature Medicine, Nov. 14, 2010, vol. 16, N. 12, pp. 1396-1399.
Extended European Search Report dated Jan. 2, 2024 for European Application No. 23183121.5.
Hirata et al., "Cold-Sensitive Corneal Afferents Respond to a Variety of Ocular Stimuli Central to Tear Production: Implications for Dry Eye Disease," Investigative Ophthalmology & Visual Science, vol. 51, No. 8, Aug. 1, 2010, pp. 3976-3976.
Robbins et al., "Menthol stimulated lacrimation and induction of Fos in the trigeminal nucleus", Program No. 761. 1BB21 2009 Neuroscience Meeting Planner. Chicago: Society for Neuroscience, 2009, Accessed on Apr. 6, 2017 at: http://www.abstractsonline.com/plan/AbstractPrintView.aspx?mID=2285&sKey=d20b9ed7-54a1-4973-abfa-026d87aaafb6&cKey=43c1e23d-3c5b-4f98-b43e-07888a763161.
McKemy, "Therapeutic potential of TRPM8 modulators", Open Drug Discovery Journal, Bentham Science Publishers B.V, NL, vol. 2, No. Special Issue 2, Jan. 1, 2010 (Jan. 1, 2010), pp. 81-88.
Sherkheli et al., "Characterization of selective TRPM8 ligands and their structure activity response (S.A.R) relationship", Journal of Pharmacy and Pharmaceutical Sciences, Canadian Society for Pharmaceutical Sciences, vol. 13, No. 2, Jul. 22, 2010 (Jul. 22, 2010), pp. 242-253.
Zholos, "Pharmacology of transient receptor potential melastatin channels in the vasculature: Vascular TRPM channels", British Journal of Pharmacology, vol. 159, No. 8, Mar. 5, 2010 (Mar. 5, 2010), pp. 1559-1571.
"Tearing (Epiphora)", In M H Beers et al.: "The Merck Manual", 2006, Merck Research Laboratories, p. 877.
Extended European Search Report dated Jan. 8, 2014 for European Application No. 11823113.3.
Moss et al., "Long-term incidence of Dry Eye in an Older Population,"Optometry and Vision Science, 2008, vol. 85, pp. 668-674.
Barker et al., "Burning mouth syndrome: an update on recent findings", Australian Dental Journal, vol. 50, 2005, pp. 220-223.
Leiblum et al., "Vaginal Dryness: A Comparison of Prevalence and Interventions in 11 countries", Journal of Sexual Medicine, vol. 6, 2009, pp. 2425-2433.
Dartt et al., "Neural Regulation of Lacrimal Gland Secretory Processes: Relevance in Dry Eye Diseases", Prog Retin Eye Res., vol. 28, 2009, pp. 155-177.
Acosta et al., "Tear Secretion Induced by Selective Stimulation of Corneal and Conjunctival Sensory Nerve Fibers", Investigative Ophthalmology & Visual Science, vol. 45, 2004, pp. 2333-2336.
Belmonte et al., "Neural basis of sensation in intact and injured corneas", Experimental Eye Research, vol. 78, 2004, pp. 513-525.
Beck et al., "Prospects for prostate cancer imaging and therapy using high-affinity TRPM8 activators", Cell Calcium, 41, 2007, pp. 285-294.
Behrendt et al., "Characterization of the mouse cold-menthol receptor TRPM8 and vanilloid receptor type-1 VR1 using a fluorometric imaging plate reader (FLIPR) assay", British Journal of Pharmacology, 141, pp. 737-745, 2004.
Bodding et al., "Characterisation of TRPM8 as pharmacophore receptor", Cell Calcium, 42, pp. 618-628, 2007.
International Search Report and Written Opinion mailed Apr. 11, 2023 for International Application Serial No. PCT/US2022/081775 filed Dec. 16, 2022.
International Search Report and Written Opinion mailed Jun. 4, 2021 for International Application Serial No. PCT/US2021/023946 filed Mar. 24, 2021.

OPHTHALMIC PHARMACEUTICAL COMPOSITIONS AND USES THEREOF

RELATED APPLICATIONS

This application is a continuation of U.S. patent application Ser. No. 18/082,844, filed Dec. 16, 2022, which claims priority of U.S. Provisional Patent Application No. 63/290,781, filed Dec. 17, 2021, the entire content of which is incorporated herein by reference.

FIELD

The present disclosure relates generally to ophthalmic pharmaceutical compositions of (1R,2S,5R)-2-isopropyl-N-(4-methoxyphenyl)-5-methylcyclohexane-1-carboxamide (WS-12) and uses thereof. The structure of WS-12 is shown below.

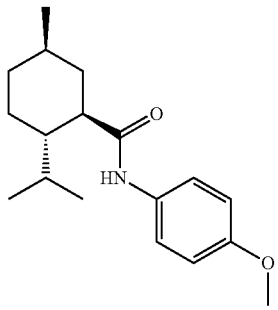

WS-12

BACKGROUND

Wetness of the ocular surface and other exposed mucosae is maintained by a continuous aqueous fluid secretion produced by exocrine glands. Disturbances of this process lead to eye, mouth and vaginal dryness syndromes that are highly prevalent, particularly among aged persons (Moss, S. E., et al. 2008. Optom. Vis. Sci. 85:668-674; Barker, K. E. & Savage, N. W. 2005. Aust. Dent. 3. 50:220-223; Leiblum, S. R., et al. 2009. 3. Sex Med 6:2425-2433). Tear flow occurring in the absence of emotional or exogenous irritant stimuli is called 'basal' tear secretion. In the eye, basal tear flow is adjusted to variations in environmental conditions and blinking rate (Dartt, D. A. 2009, Prog. Retin. Eye Res. 28:155-177). Tear production also increases markedly upon ocular surface irritation (Acosta, M. C. et al. 2004. Invest Ophthalmol. Vis. Sci. 45:2333-2336). Irritating stimuli are detected by mechano-nociceptor and polymodal nociceptor trigeminal nerve endings that are sensitive to injurious mechanical forces, noxious heat and irritant chemicals that evoke pain (Belmonte, C., et al. 2004. Exp. Eye Res. 78:513-525) and irritation-induced tear production. However, the neural structures responsible for sensing ocular surface dryness to regulate basal tear production rate remain undefined.

Dry eye, also known as xerophthalmia, is a disease characterized by persistent dryness of the conjunctiva and opacity of the cornea. As used herein, dry eye also encompasses the disorder known as meibomian gland dysfunction, or MGD.

Over 30 million people in the US alone suffer from dry eye, but less than 10% are actually treated. Moreover, prevalence of dry eye continues to rise as a result of an aging population, and more frequent use of contact lenses, computers, smartphones and tablets. It is believed that dry eye represents one of the most common diseases or disorders for which patients seek an appointment with an ophthalmologist or optometrist, and the majority of those patients do not receive a pharmaceutical intervention or punctal plugs (Stonecipher et al., *Therapeutics and Clinical Risk Management* 2013, 9:409-415).

Multiple causes can lead to dry eye, which is more common in elderly people. Among the diseases or disorders that cause or are related to dry eye are: reduced function, inflammation or obstruction of the meibomian glands, vitamin A deficit, Sjögren syndrome, rheumatoid arthritis and other rheumatologic diseases, chemical or thermal burns, or drugs such as atenolol, chlorpheniramine, hydrochlorothiazide, isotretinoin, ketorolac, ketotifen, levocabastin, levofloxacin, oxybutynin, or tolterodine.

Treatments for dry eye include the use of corticosteroids, which may be effective in early stages of the disease, vitamin A supplements and pilocarpine, which is a drug that increases tear production. Preparations such as artificial tears, solutions of hydroxypropyl methylcellulose (hypromellose) and carbomer gels are used to reduce dryness when applied to the conjunctiva. However, these treatments have clear limitations regarding their respective efficacy and toxicity.

Therefore, there is a need to provide ophthalmic pharmaceutical compositions that treat or reduce a sign or symptom of a disease or disorder that involves tear production in subject. There is also a need to provide such ophthalmic pharmaceutical compositions wherein the stability of a pharmaceutically active ingredient or ingredients contained in such an ophthalmic pharmaceutical composition is maintained in order to maximize the pharmaceutical activity of an ophthalmic pharmaceutical composition in each dose administered. What is also needed are ophthalmic pharmaceutical compositions that treat or reduce the likelihood of dry eye, as well as a sign or symptom thereof, in a subject, which does not contain a preservative that may have a deleterious effect on the subject.

WO 2012/032209 describes WS-12 an agonist of the TRPM8 calcium channel, and useful in treating xerophthalmia or dry eye. It is important to maintain the stability of WS-12 aqueous ophthalmic compositions to maximize the pharmaceutical activity of WS-12 in each dose administered. Accordingly, what is needed are ophthalmic pharmaceutical compositions comprising WS-12 in a container that can maintain stability of WS-12 with respect to increased temperature, humidity, and exposure to light (and particularly to ultraviolet light), among other types of external effects.

The citation of any reference herein should not be deemed as an admission that such reference is available as prior art to the present disclosure.

SUMMARY

Provided herein are new and useful ophthalmic pharmaceutical compositions for: (a) the treatment or reduction of the likelihood of an ophthalmic disease or disorder that involves tear production in a subject, e.g. dry eye; (b) the treatment or reduction of a sign or symptom of such an ophthalmic disease or disorder, or (c) a combination of (a) and (b). Also provided is a method for treating an ophthalmic disease or disorder that involves tear production in a subject and/or treating or reducing a sign or symptom of such an ophthalmic disease or disorder.

Broadly, the present disclosure extends to ophthalmic pharmaceutical compositions, comprising about 0.0005% w/v to about 0.01% w/v (1R,2S,5R)-2-isopropyl-N-(4-methoxyphenyl)-5-methylcyclohexane-1-carboxamide (WS-12) or a pharmaceutically acceptable salt thereof, about 0.1% w/v to about 5% w/v of a solubilizing agent, about 0.1% w/v to about 0.5% w/v of a viscosity modifier, about 0.3% w/v to about 1% w/v of a buffer, and about 0.1% w/v to about 1.0% w/v of a tonicity agent.

The pH of an ophthalmic pharmaceutical composition of the present disclosure can range from about pH 5.0 to about 8.5. More particularly, the pH of an ophthalmic pharmaceutical composition of the present disclosure can range from about 6.7 to about 7.3. In a particular embodiment, the pH of an ophthalmic pharmaceutical composition of the present disclosure is about 7. An ophthalmic pharmaceutical composition of the present disclosure can further comprise a pH adjuster in order to obtain the desired pH. Numerous pH adjusters have applications, including a pH adjuster in an ophthalmic pharmaceutical composition of the present disclosure. A particular example of a pH adjuster having applications in an ophthalmic pharmaceutical composition of the present disclosure is sodium hydroxide (e.g., 1 N sodium hydroxide). In order to adjust the pH to about 7 a sufficient quantity of 1 N sodium hydroxide is added.

Moreover, solubilizers having applications in ophthalmic pharmaceutical compositions of the present disclosure include polyethylene glycol (PEG) 400, castor oil, polyoxyethylene (20) sorbitan mono-oleate (TWEEN 80), polyoxyl 35 castor oil (KOLLIPHOR® EL), and purified polyoxyl 35 castor oil (KOLLIPHOR® ELP), as well as any combination thereof. In a particular embodiment, the solubilizer is polyoxyl 35 castor oil (KOLLIPHOR® EL).

According to the Joint FAO/WHO Expert Committee on Food Additives (JECFA), WS-12 is insoluble in water, and only sparingly soluble in avocado oil or ethanol. Unpredictably, certain excipients failed to satisfactorily solubilize the active agent WS-12, including polyvinylpyrrolidone (PVP), propylene glycol, and ethylene oxide-formaldehyde-para-octylphenol copolymer (Tyloxapol), whereas others satisfactorily solubilized the active agent WS-12, including polyethylene glycol (PEG) 400, castor oil, polyoxyethylene (20) sorbitan mono-oleate (TWEEN 80), polyoxyl 35 castor oil (KOLLIPHOR® EL or KOLLIPHOR® ELP). In some embodiments, the compositions provided herein comprise about 1.5 to about 5 w/v % polyethylene glycol 400. In some embodiments, the compositions provided herein comprise about 1 w/v % castor oil. In some embodiments, the compositions provided herein comprise about 0.1 to about 4 w/v % polyoxyethylene (20) sorbitan mono-oleate. In some embodiments, the compositions provided herein comprise about 1 to about 5 w/v % of a polyoxyl 35 castor oil.

What is more, a variety of viscosity modifiers can readily be used in an ophthalmic pharmaceutical composition of the present disclosure, such as a cellulose derivative, a clay, aluminum or magnesium silicate, a natural gum, a synthetic polymer; colloidal silicon dioxide, a silicate, to name only a few, as well as any combination thereof. Particular examples of a cellulose derivative having applications in an ophthalmic pharmaceutical composition of the present disclosure include, but certainly are not limited to methylcellulose, microcrystalline cellulose, carboxymethylcellulose, ethylcellulose, hydroxyethylcellulose, hydroxypropyl cellulose, and hydroxypropyl methylcellulose. Likewise, several clays can also be used, such as hectorite, bentonite, aluminum and/or magnesium silicate, and kaolin. Natural gums that have applications in an ophthalmic pharmaceutical composition of the present disclosure comprise acacia, guar gum, tragacanth, xanthan gum, alginate, carrageenan, locust bean gum, or any combination thereof. In a particular embodiment of an ophthalmic pharmaceutical composition of the present disclosure, the viscosity modifier is hydroxypropyl methylcellulose (hypromellose).

Moreover, in an ophthalmic pharmaceutical composition of the present disclosure, a particular tonicity agent having applications is sodium chloride.

Numerous buffers have applications in an ophthalmic pharmaceutical composition of the present disclosure. Examples include, but certainly are not limited to phosphate buffers, citrate buffers, TRIS Base, TRIS HCl, PBS, HEPES, MES, PIPES, and TES. Other buffer examples include boric acid. In some embodiments, the buffer comprises a phosphate.

An ophthalmic pharmaceutical composition of the present disclosure further comprises purified water.

Similarly, a particular example of an ophthalmic pharmaceutical composition of the present disclosure comprises:
 (a) about 0.003% w/v (1R,2S,5R)-2-isopropyl-N-(4-methoxyphenyl)-5-methylcyclohexane-1-carboxamide;
 (b) about 0.14% w/v hypromellose;
 (c) about 3.0% w/v polyoxyl 35 castor oil;
 (d) about 0.78% w/v a phosphate buffer (e.g., a sodium phosphate buffer, e.g., monosodium phosphate or sodium dihydrogen phosphate dihydrate)
 (e) about 0.55% w/v NaCl;
 (f) a sufficient amount of NaOH (e.g., 1 N NaOH) to provide an ophthalmic pharmaceutical composition with a pH of about 7; and
 (g) purified water.

Another example of an ophthalmic pharmaceutical composition of the present disclosure comprises:
 (a) 0.003±15% w/v (1R,2S,5R)-2-isopropyl-N-(4-methoxyphenyl)-5-methylcyclohexane-1-carboxamide;
 (b) 0.14±15% w/v hypromellose;
 (c) 3.0±15% w/v polyoxyl 35 castor oil;
 (d) 0.78±15% w/v a phosphate buffer (e.g., a sodium phosphate buffer, e.g., monosodium phosphate or sodium dihydrogen phosphate dihydrate)
 (e) 0.55±15% w/v NaCl;
 (f) a sufficient amount of NaOH (e.g., 1 N NaOH) to provide an ophthalmic pharmaceutical composition with a pH of about 7; and
 (g) purified water.

Another example of an ophthalmic pharmaceutical composition of the present disclosure comprises:
 (a) 0.003±10% w/v (1R,2S,5R)-2-isopropyl-N-(4-methoxyphenyl)-5-methylcyclohexane-1-carboxamide;
 (b) 0.14±10% w/v hypromellose;
 (c) 3.0±10% w/v polyoxyl 35 castor oil;
 (d) 0.78±10% w/v a phosphate buffer (e.g., a sodium phosphate buffer, e.g., monosodium phosphate or sodium dihydrogen phosphate dihydrate)
 (e) 0.55±10% w/v NaCl;
 (f) a sufficient amount of NaOH (e.g., 1 N NaOH) to provide an ophthalmic pharmaceutical composition with a pH of about 7; and
 (g) purified water.

Yet another example of an ophthalmic pharmaceutical composition of the present disclosure comprises:

(a) about 0.0014% w/v (1R,2S,5R)-2-isopropyl-N-(4-methoxyphenyl)-5-methylcyclohexane-1-carboxamide;
(b) about 0.14% w/v hypromellose;
(c) about 3.0% w/v polyoxyl 35 castor oil;
(d) about 0.78% w/v a phosphate buffer (e.g., a sodium phosphate buffer, e.g., monosodium phosphate or sodium dihydrogen phosphate dihydrate)
(e) about 0.55% w/v NaCl;
(f) a sufficient amount of NaOH (e.g., 1 N NaOH) to provide an ophthalmic pharmaceutical composition with a pH of about 7; and
(g) purified water.

Another example of an ophthalmic pharmaceutical composition of the present disclosure comprises:
(a) about 0.0014±15% w/v (1R,2S,5R)-2-isopropyl-N-(4-methoxyphenyl)-5-methylcyclohexane-1-carboxamide;
(b) about 0.14±15% w/v hypromellose;
(c) about 3.0±15% w/v polyoxyl 35 castor oil;
(d) about 0.78±15% w/v a phosphate buffer (e.g., a sodium phosphate buffer, e.g., monosodium phosphate or sodium dihydrogen phosphate dihydrate)
(e) about 0.55±15% w/v NaCl;
(f) a sufficient amount of NaOH (e.g., 1 N NaOH) to provide an ophthalmic pharmaceutical composition with a pH of about 7; and
(g) purified water.

Another example of an ophthalmic pharmaceutical composition of the present disclosure comprises:
(a) about 0.0014±10% w/v (1R,2S,5R)-2-isopropyl-N-(4-methoxyphenyl)-5-methylcyclohexane-1-carboxamide;
(b) about 0.14±10% w/v hypromellose;
(c) about 3.0±10% w/v polyoxyl 35 castor oil;
(d) about 0.78±10% w/v a phosphate buffer (e.g., a sodium phosphate buffer, e.g., monosodium phosphate or sodium dihydrogen phosphate dihydrate)
(e) about 0.55±10% w/v NaCl;
(f) a sufficient amount of NaOH (e.g., 1 N NaOH) to provide an ophthalmic pharmaceutical composition with a pH of about 7; and
(g) purified water.

In addition, the present disclosure further extends to various methods for treating various ophthalmic diseases or disorders, and/or signs or symptoms associated with such diseases or disorders, with an ophthalmic pharmaceutical composition disclosed herein.

In particular, the present disclosure extends to a method for treating an ophthalmic disease or disorder involving tear production and/or reducing the signs or symptoms thereof, comprising administering a therapeutically effective amount of an ophthalmic pharmaceutical composition of the present disclosure. In a specific embodiment, the ophthalmic disease or disorder is dry eye.

The present disclosure further extends to a method for treating or reducing ocular irritation involving tear production in a subject in need thereof, comprising administering a therapeutically effective amount of an ophthalmic pharmaceutical composition of the present disclosure Also provided is a method for treating or reducing a sign or symptom of an ophthalmic disease or disorder in a subject in need thereof, comprising administering a therapeutically effective amount of an ophthalmic pharmaceutical composition of the present disclosure. Thus, a method of the present disclosure readily has applications in treating or reducing a sign or symptom of an ophthalmic disease or disorder such as dry eye. Examples of such symptoms of dry eye that can be readily treated or reduced with a therapeutically effective amount of an ophthalmic pharmaceutical composition of the present disclosure include a decrease in visual analog scale (VAS) symptom score (ocular discomfort score [ODS], eye dryness score or ocular pain score) or a decrease in scores obtained from the "Symptom Assessment In Dry Eye" questionnaire disclosed and validated in Schaumberg et al., "Global Dry Eye Symptom Index", The Ocular Surface, 5(1):50-57 (2007), and which was designed to quantify the frequency and severity of symptoms of dry eye syndrome based upon a visual analog scale (the SANDE questionnaire), eye dryness, and ocular pain or irritation, to name only a few. Likewise, signs of dry eye that can be treated or reduced with an ophthalmic pharmaceutical composition of the present disclosure include, but are not limited to, Schirmer Score (unanesthetized and anesthetized), ocular surface staining, conjunctival redness, tear film break-up time, and tear production. The Schirmer test, first disclosed in 1903 by Otto Schirmer, is designed to test whether a subject's eye produces sufficient tears to keep the eye moist (Schirmer O, Studien zur Physiologie und Pathologie der Tranenabsonderung und Tranenbfuhr (Arch. Klin. Opthalmol. 56:197-291 (1903)). Thus, this test is concerned with determining whether the subject produces a sufficient amount of tears to lubricate the eye. Ocular staining is also used as a sign for dry eye disease or disorder. In ocular surface staining, a dye is placed on the surface of the eye in order to uncover abnormalities on the surface of the eye. Once a dye is placed upon the eye, the pattern of staining observed using the dye is recorded, usually via imaging. The imaged staining pattern can then be used to diagnose the presence and severity of dry eye. Numerous dyes have applications in ocular surface staining, including but not limited to Rose Bengal, lissamine green, and fluorescein, to name only a few.

These and other aspects of the present disclosure will be better appreciated by reference to the following drawings and Detailed Description.

DETAILED DESCRIPTION

Figure 1:
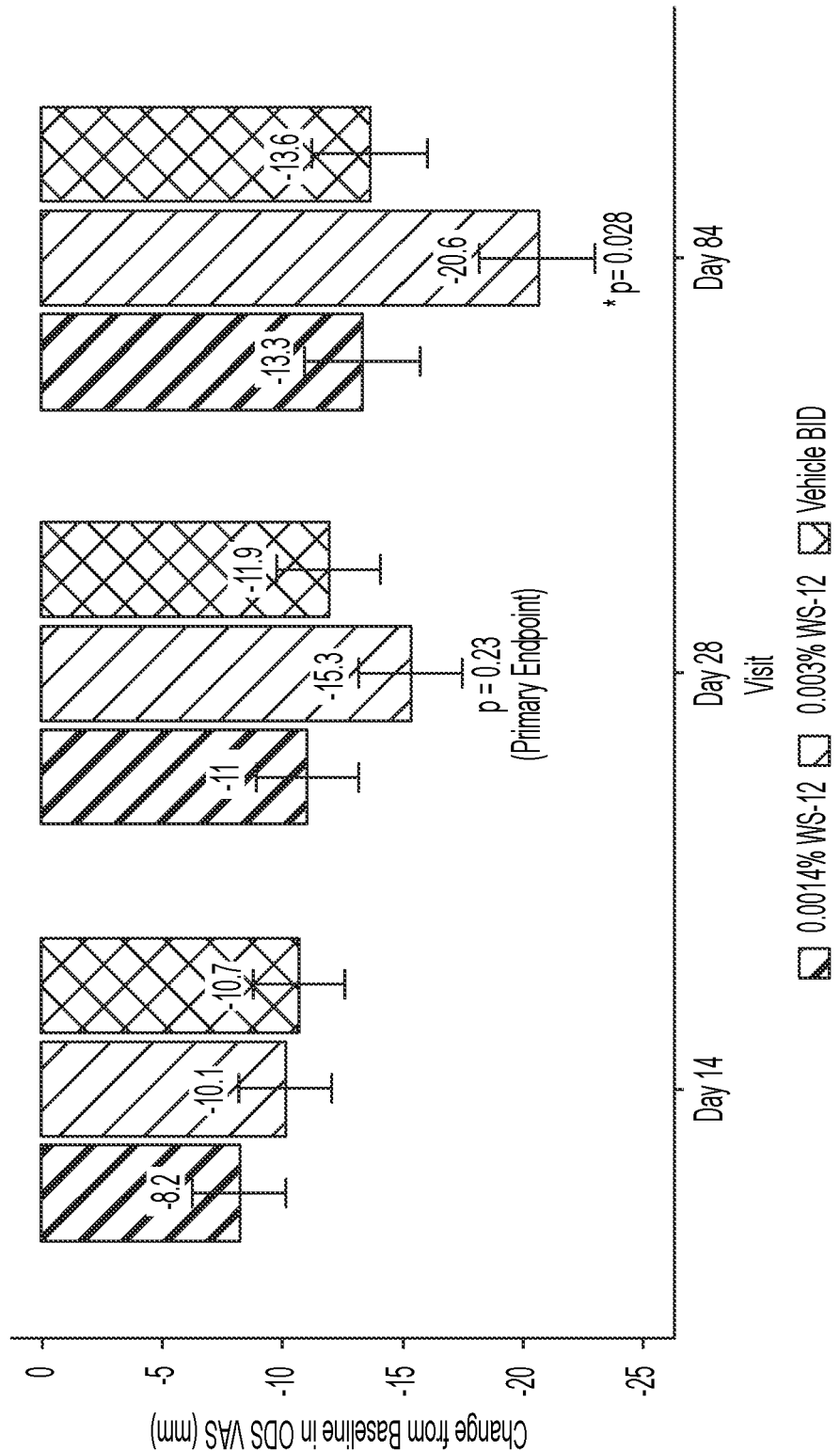
FIG. 1 is a bar graph setting forth changes reported in ocular discomfort (ODS-VAS) of subjects administered a therapeutically effective amount of an ophthalmic pharmaceutical composition of the instant disclosure (*=p<0.05).

The present disclosure is, in part, based on the discovery that surprisingly and unexpectedly, WS-12 can be sufficiently solubilized in an ophthalmic pharmaceutical composition of the present disclosure such that upon delivery to a subject, WS-12 is readily bioavailable. Moreover, an ophthalmic pharmaceutical composition of the present disclosure does not require a preservative, for example benzalkonium chloride. The ophthalmic pharmaceutical compositions of the present disclosure may be provided as aqueous solutions.

Thus, the present disclosure provides ophthalmic pharmaceutical compositions, comprising about 0.0005% w/v to about 0.01% w/v (1R,2S,5R)-2-isopropyl-N-(4-methoxyphenyl)-5-methylcyclohexane-1-carboxamide (WS-12) or a pharmaceutically acceptable salt thereof, about 0.1% w/v to about 5% w/v of a solubilizing agent, about 0.1% w/v to about 0.5% w/v of a viscosity modifier, about 0.3% w/v to about 1% w/v of a buffer, and about 0.1% w/v to about 1.0% w/v of a tonicity agent.

In some embodiments, an ophthalmic pharmaceutical composition comprises:
  (a) about 0.0005, 0.00076, 0.0008, 0.001, 0.0014, 0.0015, 0.001519, 0.002, 0.003, 0.003039, 0.004, 0.005, 0.006, 0.006078, 0.007, 0.008, 0.009, or 0.009116% w/v (1R, 2S,5R)-2-isopropyl-N-(4-methoxyphenyl)-5-methylcyclohexane-1-carboxamide (WS-12) or a pharmaceutically acceptable salt thereof;
  (b) about 0.1, 0.2, 0.3, 0.4, 0.5, 1, 1.5, 2, 2.0, 2.00, 3, 3.0, 3.00, 4, 4.0, 4.00, 5, 5.0, or 5.00% w/v of a solubilizing agent (e.g., polyethylene glycol (PEG) 400, castor oil, polyoxyethylene (20) sorbitan mono-oleate (TWEEN 80), polyoxyl 35 castor oil (KOLLIPHOR® EL or KOLLIPHOR® ELP)).
  (c) about 0.1, 0.14, 0.2, 0.3, 0.4, 0.45, or 0.5% w/v of a viscosity modifier (e.g., hypromellose);
  (d) about 0.3, 0.31, 0.4, 0.5, 0.6, 0.7, 0.78, 0.8, 0.9, 1, or 1.0% w/v of a buffer (e.g., monosodium phosphate); and
  (e) about 0.1, 0.2, 0.3, 0.4, 0.49, 0.5, 0.55, 0.6, 0.7, 0.71, 0.8, or 0.9% w/v of a tonicity agent (e.g., sodium chloride).

Additionally, it has been found that WS-12, e.g., in a composition comprising WS-12, undergoes sorption with the polyolefin material in which it is contained. Such sorption characteristics, e.g., adsorption, absorption, or both, create uncertainty regarding the long-term concentration stability of WS-12 stored in such a material. A process has been discovered for stabilizing WS-12-containing compositions disposed within a polymeric (e.g., plastic, e.g., polyolefin) container, which includes exposing the WS-12 composition in its container to a temperature above about 20-25° C. (e.g., at about 40° C.) for at least about 1, 2, 3, 4, 5, 6, 7, 8, 9, or 10 days up to about two weeks. It has been discovered that this process reduces the variance of WS-12 concentration when subsequently stored at 20-25° C. for about 7, 14, 90, 140, 150, 160, 180, 365, or more days. For example, such WS-12 concentration variance is limited to a decrease of not more than about 6% w/v of WS-12 during storage (e.g., at or below ambient temperature of about 20-25° C.) subsequent to the heat treatment process. One advantage of such a process is that the compositions provided herein may be stored at ambient temperature without need for refrigerated storage. The benefits of such storage conditions are readily apparent, and include ease of storage and transport, in particular to residential or geographic locations where electricity or refrigeration is either unreliable or unavailable.

Thus, also provided herein are processes for preparing an article of manufacture, wherein the article comprises a composition provided herein in a polymeric container, wherein the processes include maintaining the article at a first temperature of about 35-45° C. (e.g., at about 40° C.). The article may subsequently be stored at a second temperature of at or below ambient temperature, e.g., at or below about 20-25° C., e.g., without refrigeration. Accordingly, the WS-12 composition in the article (e.g., the WS-12 aqueous composition in fluid contact with its polymeric container) has a WS-12 concentration variance of less than about 6% w/v during storage at the second temperature. In some embodiments, the concentration variance of WS-12 is less than about 5% w/v, less than about 4% w/v, less than about 3% w/v, or less than about 2% w/v. It is understood that % w/v herein may correspond to % as determined by liquid chromatography (LC; e.g., high performance LC (HPLC)). In some embodiments, storage of the article at the second temperature includes at least about 7, 14, 90, 140, 150, 160, 180, 365, or more days, e.g., at least about 1, 2, 4, 12, 20, 30, 52, or more weeks, e.g., at least about 1, 3, 6, 9, or 12 months, e.g., at least about one half of a year, one year, or more.

The present disclosure also extends to methods of treating or reducing ocular irritation involving tear production in a subject in need thereof, treating or reducing at least one sign or symptom of an ophthalmic disease or disorder involving tear production.

Unless defined otherwise, all technical and scientific terms used herein have the same meanings as commonly understood by one of ordinary skill in the art to which this disclosure belongs. Although any methods and materials similar or equivalent to those described herein can be used in the practice or testing of the present disclosure.

All numerical designations, e.g., volume, mass, etc. are approximations which are varied by (+) or (−) by increments of 1.0 or 0.1, as appropriate. It is to be understood, although not always explicitly stated, that all numerical designations are preceded by the term "about".

Numerous terms and phrases are used throughout the instant specification and claims and are defined below.

"About" and "approximately" are interchangeable and mean plus or minus a percent (e.g., ±5%) of the number, parameter, or characteristic so qualified, which would be understood as appropriate by a skilled artisan to the scientific context in which the term is utilized.

As used here, the singular form "a", "an" and "the" include plural reference unless the context clearly dictates otherwise.

As used herein, the terms "comprising", "comprises" and "comprise" are intended to mean that the compositions, preparations and methods disclosed herein include recited elements, but do not exclude others.

As used herein, the phrase "pH modifier" refers to an excipient used in a pharmaceutical composition that, due to its cationic or anionic properties, helps to control and maintain the pharmaceutical composition at a desired pH.

As used herein, the phrase "ophthalmic disease or disorder" refers to a disease or disorder of the eye.

As used herein a "sign" of a disease or disorder is objective evidence of a disease that can be observed or measured.

As used herein, a "symptom" of a disease or disorder is the subjective experience of a potential health issue, which cannot be observed by a clinician or anyone other than the person experiencing the symptom.

The term "therapeutically effective amount" as used herein refers to an amount of an agent needed to treat, ameliorate, or prevent the targeted disease or disorder, or to exhibit a detectable therapeutic or preventative effect on the targeted disease or disorder, or a sign or symptom associated with the targeted disease or disorder. In general, the therapeutically effective amount can be estimated initially either in cell culture assays or in animal models, for example, in non-human primates, mice, rabbits, dogs, or pigs. The animal model may also be used to determine the appropriate concentration range and route of administration. Such information can then be used to determine useful doses and routes for administration in humans. For an ophthalmic pharmaceutical composition of the present disclosure, a therapeutically effective dose or amount can be estimated initially using a variety of techniques well-known in the art. Initial doses used in animal studies may be based on effective concentrations established in cell culture assays. Dosage ranges appropriate for human subjects can be determined, for example, using data obtained from animal studies, cell culture assays, and clinical trials with humans.

Compositions

Ophthalmic pharmaceutical compositions of the present disclosure can be formulated in various dosage forms according to a known method described, for example, in the Japanese Pharmacopoeia, Seventeenth Edition, General Rules for Preparation or the like. Examples of the dosage form include injection, eye drop, eye ointment, ear drop, topical liquid, spray, ointment, gel, and syrup. From the viewpoint of advantageously utilizing the pharmacological actions of WS-12, the dosage form is preferably, a dosage form for eye disease, specifically, eye drop or eye ointment, and particularly preferably, eye drop. Thus, in some embodiments, an ophthalmic pharmaceutical composition of the present disclosure can be administered topically to an eye of a subject.

Optionally, ophthalmic pharmaceutical compositions of the present disclosure can comprise one or more additional active pharmaceutical ingredients, depending upon the ophthalmic disease or disorder for which an ophthalmic pharmaceutical composition is to be used to treat or reduce a sign or symptom of a disease or disorder that involves tear production in subject. Examples include, but are not limited to: α1 receptor blockers (including bunazosin or a salt thereof or a solvate thereof such as bunazosin hydrochloride); α2 receptor agonists (including brimonidine or a salt thereof or a solvate thereof such as brimonidine tartrate, and apraclonidine or a salt thereof or a solvate thereof); β-blockers (including carteolol or a salt thereof or a solvate thereof such as carteolol hydrochloride, nipradilol or a salt thereof or a solvate thereof, timolol or a salt thereof or a solvate thereof such as timolol maleate, betaxolol or a salt thereof or a solvate thereof such as betaxolol hydrochloride, levobunolol or a salt thereof or a solvate thereof such as levobunolol hydrochloride, befunolol or a salt thereof or a solvate thereof, atenolol or a salt thereof or a solvate thereof, and metipranolol or a salt thereof or a solvate thereof); carbonic anhydrase inhibitors (including dorzolamide or a salt thereof or a solvate thereof such as dorzolamide hydrochloride, brinzolamide or a salt thereof or a solvate thereof, acetazolamide or a salt thereof or a solvate thereof, dichlorphenamide or a salt thereof or a solvate thereof, and methazolamide or a salt thereof or a solvate thereof); prostaglandins (including their analogs and derivatives (e.g., prostaglandin F2α derivatives) including isopropyl unoprostone or a solvate thereof, tafluprost or a solvate thereof, travoprost or a solvate thereof, bimatoprost or a solvate thereof, latanoprost or a solvate thereof, cloprostenol or a solvate thereof, and fluprostenol or a solvate thereof); Rho kinase inhibitors (including Netarsudil, Ripasudil or a salt thereof or a solvate thereof, Y-39983, and H-1129); sympathomimetic drugs (including dipivefrine or a salt thereof or a solvate thereof such as dipivefrin hydrochloride, and epinephrine or a salt thereof or a solvate thereof such as epinephrine, epinephrine borate, or epinephrine hydrochloride); parasympathomimetic drugs (including distigmine bromide or a salt thereof or a solvate thereof, pilocarpine or a salt thereof or a solvate thereof such as pilocarpine, pilocarpine hydrochloride or pilocarpine nitrate, and carbachol or a salt thereof or a solvate thereof); calcium antagonists (including lomerizine or a salt thereof or a solvate thereof such as lomerizine hydrochloride); and cholinesterase inhibitors (including demecarium or a salt thereof or a solvate thereof, echothiophate or a salt thereof or a solvate thereof, and physostigmine or a salt thereof or a solvate thereof). These APIs can be mixed with WS-12 in an ophthalmic pharmaceutical composition of the present disclosure singly, or as combinations of two or more.

As explained above, numerous solubilizers have applications in an ophthalmic pharmaceutical composition of the present disclosure. As used herein, the term "solubilizer" with respect to a pharmaceutical composition refers to an excipient that increases the solubility of the active pharmaceutical ingredient (API) in water. WS-12, which is an API in an ophthalmic pharmaceutical composition of the present disclosure, is insoluble in water. Thus, to increase its solubility in water, and consequently ensure its bioavailability is therapeutically effective upon delivery, a solubilizer may be added to an ophthalmic pharmaceutical composition of the present disclosure. Examples of solubilizers having applications in an ophthalmic pharmaceutical composition of the present disclosure include polyethylene glycol (PEG) 400, castor oil, polyoxyethylene (20) sorbitan mono-oleate (TWEEN 80), polyoxyl 35 castor oil (KOLLIPHOR® EL or KOLLIPHOR® ELP), as well as any combination thereof. In a particular embodiment, the solubilizer is polyoxyl 35 castor oil.

A micelle or micella (plural micelles or micellae, respectively) is an aggregate of surfactant molecules dispersed in a liquid, forming a colloidal suspension. A typical micelle in water forms an aggregate with the hydrophilic "head" regions in contact with surrounding solvent, sequestering the hydrophobic single-tail regions in the micelle's center. Without being bound by theory, it is thought that this phase is caused by the packing behavior of single-tail lipids in a bilayer. The difficulty filling all the volume of the interior of a bilayer (e.g., in a liposome), while accommodating the area per head group forced on the molecule by the hydration of the lipid head group, leads to the formation of the micelle. This type of micelle is known as a normal-phase micelle (oil-in-water micelle). Inverse micelles have the head groups at the center with the tails extending out (water-in-oil micelle). Micelles are approximately spherical in shape. Other phases, including shapes such as ellipsoids, cylinders, and bilayers, are also possible. The shape and size of a micelle are a function of the molecular geometry of its surfactant molecules and solution conditions such as surfactant concentration, temperature, pH, and ionic strength. The process of forming micelles is known as micellization, and forms part of the phase behavior of many lipids according to their polymorphism. When surfactants are present above their critical micelle concentration (CMC), they can act as emulsifiers that will allow a compound that is normally insoluble (in the solvent being used) to dissolve. This occurs because the insoluble species can be incorporated into the micelle core, which is itself solubilized in the bulk solvent by virtue of the head groups' favorable interactions with solvent species.

Thus, in some embodiments, the solubilizer has a CMC of about less than 0.1% w/w at 37° C. In some embodiments, the solubilizer which is polyoxyl 35 castor oil has a CMC of about 0.02% w/w at 37° C. In some embodiments, upon heating neat solubilizer the last solid constituents of the polyoxyl 35 castor oil melt at about 26° C. to yield a clear oily liquid. In some embodiments, the solubilizer is present at or above its CMC value. In some embodiments, the compositions herein include at least a portion of the WS-12 encapsulated within micelles of the solubilizer. In some embodiments, more than 50%, e.g., at least 60%, at least 70%, at least 80%, at least 90%, at least 95%, at least 98%, at least 99%, or more, or essentially all, of the WS-12 present in the composition is encapsulated within micelles of the solubilizer. In some embodiments, the micelles have an average diameter of about 2 to about 20 nm. In some embodiments, the micelles have an average diameter of about 4 to about 10 nm. In some embodiments, the micelles have an average diameter of about 5 nm±2 nm. In some embodiments, the micelles have an average diameter of 5 nm±0.5 nm. Accordingly, in some embodiments, WS-12 is entrapped within micelles having an average diameter of about 2, 3, 4, 5, 6, 7, 8, 9, 10, 11, 12, 13, 14, 15, 16, 17, 18, 19, or 20±0.5 nm. In some embodiments, the micelles are unilamellar. In some embodiments, the micelles are spherical, such as when the surfactant as at a concentration at or above its CMC. In some embodiments, the surfactant forms cylindrical micelles or other aggregated phases (e.g., hexagonal phase, cubic phase, or lamellar phase) when the surfactant is at a still higher concentration above the surfactant's CMC. In some embodiments, the surfactant forms a multilamellar liposome. In some embodiments, the WS-12 in the compositions provided herein has a concentration of up to about 200 µM.

In addition, numerous viscosity modifiers readily have applications in an ophthalmic pharmaceutical composition of the present disclosure. As used herein, the phrase "viscosity modifier" with respect to a pharmaceutical composition refers to an excipient that is intended to change the thickness or texture of a pharmaceutical composition. They include thickeners, gelation agents, and stiffening agents used to convert liquids to gels, pastes or powders to aid formulators in creating the ideal product for the end-user. They can also modify the thickness of a liquid. Viscosity modifiers having applications in an ophthalmic pharmaceutical composition of the present disclosure include a cellulose derivative (e.g. methylcellulose, microcrystalline cellulose, carboxymethylcellulose, ethylcellulose, hydroxyethylcellulose, hydroxypropyl cellulose, hydroxypropyl methylcellulose, or any combination thereof); a clay (e.g. hectorite, bentonite, aluminum and/or Mg silicate, kaolin, or any combination thereof); a natural gum (e.g. acacia, guar gum, tragacanth, xanthan gum, alginate, carrageenan, locust bean gum, or any combination thereof); a synthetic polymer; colloidal silicon dioxide; or any combination thereof. In a particular embodiment of an ophthalmic pharmaceutical composition of the present disclosure, the viscosity modifier is hydroxypropyl methylcellulose.

As explained herein, an ophthalmic pharmaceutical composition of the present disclosure comprises a tonicity agent. The term "tonicity" refers to the measure of the effective osmotic pressure gradient; the water potential of two solutions separated by a semipermeable cell membrane. It depends on the relative concentration of selectively membrane permeable solutes across a cell membrane, which determines the direction and extent of osmotic flux. Thus, to prevent osmotic shock to the target cells of an ophthalmic pharmaceutical composition of the present disclosure, a tonicity agent such as dextrose, glycerin, mannitol, potassium chloride, sodium chloride, or any combination thereof, is included. In a particular example, the tonicity agent is sodium chloride.

The pH of an ophthalmic pharmaceutical composition of the present disclosure ranges from about 5.0 to about 8.5, and more particularly from about 6.7 to about 7.3. In a particular embodiment, an ophthalmic pharmaceutical composition of the present disclosure has a pH of about 7. A pH modifier readily has applications in an ophthalmic pharmaceutical composition of the present disclosure in order to provide the composition with the desired pH. Examples of pH modifiers having applications herein include, but certainly are not limited to include soda ash, sodium hydroxide, sodium silicate, sodium phosphates, lime, sulfuric acid, and hydrofluoric acid, to name only a few. In a particular ophthalmic pharmaceutical composition of the present disclosure, the pH modifier used is 1N sodium hydroxide and the desired pH is about 7.

An ophthalmic pharmaceutical composition of the present disclosure further comprise a buffer, such as phosphate buffers, citrate buffers, TRIS base, TRIS HCl, PBS, HEPES, MES, PIPES, or TES, to name only a few. Phosphate buffer is a particular buffer having applications in an ophthalmic pharmaceutical composition disclosed herein.

Particular examples of ophthalmic pharmaceutical compositions of the present disclosure are set forth in Table 1 below.

TABLE 1

Ingredients of WS-12 Ophthalmic Pharmaceutical Compositions

| Component | Formulation Function | 1 Qty. (% w/v) | 2 Qty. (% w/v) | 3 Qty. (% w/v) | 4 Qty. (% w/v) | 5 Qty. (% w/v) |
|---|---|---|---|---|---|---|
| WS-12 | Active Ingredient | 0.003 | 0.0014 | 0.0015 | 0.0008 | 0.0061 |
| Hypromellose (METHOCEL F4M) | Viscosity Modifier | 0.14 | 0.14 | 0.45 | 0.45 | 0.45 |
| Polyoxyl 35 Castor Oil (KOLLIPHOR EL) | Active Ingredient Solubilizing Agent | 3.00 | 3.00 | 3.00 | 3.00 | 4.00 |
| Sodium Dihydrogen Phosphate Dihydrate | Buffer | 0.78 | 0.78 | 0.78 | 0.78 | 0.78 |
| Sodium Chloride | Tonicity Agent | 0.55 | 0.55 | 0.55 | 0.55 | 0.49 |
| Sodium Hydroxide[1] | pH Adjuster | q.s. to pH 7 | q.s. to pH 7 | q.s. to pH 7 | q.s. to pH 7 | q.s. to pH 7 |
| Purified Water | Solvent | q.s. | q.s. | q.s. | q.s. | q.s. |

| Formulation Component | 6 Qty. (% w/v) | 7 Qty. (% w/v) | 8 Qty. (% w/v) | 9 Qty. (% w/v) | 10 Qty. (% w/v) | 11 Qty. (% w/v) |
|---|---|---|---|---|---|---|
| WS-12 | 0.003 | 0.0015 | 0.0091 | 0.0061 | 0.003 | 0.0015 |
| Hypromellose | 0.45 | 0.45 | 0.45 | 0.45 | 0.45 | 0.45 |
| Polyoxyl 35 Castor Oil | 4.00 | 4.00 | 4.00 | 4.00 | 2.00 | 2.00 |
| Sodium Dihydrogen Phosphate Dihydrate | 0.78 | 0.78 | 0.78 | 0.31 | 0.31 | 0.31 |
| Sodium Chloride | 0.49 | 0.49 | 0.49 | 0.71 | 0.71 | 0.71 |
| Sodium Hydroxide[1] | q.s. to pH 7 | q.s. to pH 7 | q.s. to pH 7 | q.s. to pH 7 | q.s. to pH 7 | q.s. to pH 7 |
| Purified Water | q.s. | q.s. | q.s. | q.s. | q.s. | q.s. |

[1]1N Solution, as needed.

Methods

As explained above, the present disclosure extends to various methods for treating, reducing, ameliorating, reducing the likelihood of, or preventing an ophthalmic disease or disorder, a sign or symptom of such a disease or disorder, or a combination thereof, in a subject in need of such a method. In a particular embodiment, the disease or disorder involves tear production, such as dry eye (xerophthalmia), keratoconjunctivitis sicca, or Sjögren's syndrome. Thus, the present disclosure extends to a method for treating or reducing the likelihood of dry eye in a subject, comprising administering a therapeutically effective amount of an ophthalmic pharmaceutical composition of the present disclosure.

Applicable ophthalmic diseases or disorders for which an ophthalmic pharmaceutical composition or a method of the present disclosure can be used to treat, ameliorate or prevent are not limited. A specific disease or disorder that can be prevented or treated with an ophthalmic pharmaceutical composition or a method of the present disclosure includes but certainly is not limited to dry eye or Sjögren's syndrome. The term "dry eye" is understood according to the recently reviewed definition of dry eye provided by TFOS DEWS II (. Dry eye disease (DED), also called "dry eye syndrome" or "keratoconjunctivitis sicca", is a multifactorial disease of the ocular surface characterized by a loss of homeostasis of the tear film, and accompanied by ocular symptoms, in which tear film instability and hyperosmolarity, ocular surface inflammation and damage, and neurosensory abnormalities play etiological roles (Craig et al., The Ocular Surface 2017, 15, 276-283). Dry eye occurs when either the eye does not produce enough tears or when the tears evaporate too quickly. Multiple causes can lead to dry eye, which is more common in elderly people. Causes of dry eye include but are not limited to: MGD and other ocular inflammatory processes, vitamin A deficiency, Sjögren's syndrome, rheumatoid arthritis and other rheumatological disease and disorders, chemical or thermal burns, drugs such as atenolol, chlorpheniramine, diuretics, hydrochlorothiazide, isotretinoin, ketorolac, ketotifen, levocabastin, levofloxacin, oxybutynin, and tolterodine. Sjögren's syndrome is an immune disorder characterized by a dry mouth and/or dry eyes.

Optionally, an ophthalmic pharmaceutical composition of the present disclosure can be stored in a package that blocks transmittance of light, and in particular light having a wavelength ranging from about 1 nm to about 340 m, such as ultraviolet light. Such a package may include as a primary package, such as a container that is opaque or transparent with respect to visible light. Optionally a package, and particular at least one of a primary or secondary package of an ophthalmic pharmaceutical composition of the present disclosure can comprise at least one substance that blocks transmittance of ultraviolet light. Examples of such packages as well as UV light blocking substances having applications in such packages are disclosed in published PCT application WO/2021/195256, which is hereby incorporated by reference in its entirety. In some embodiments, an ophthalmic pharmaceutical composition provided herein may be prepared and placed in a container for storage at ambient or elevated temperature. When stored in a polyolefin plastic container as compared to a polyvinyl chloride plastic container, any discoloration of the composition that may occur may be reduced. Without wishing to be bound by theory, a container having applications herein may reduce exposure of the container's contents to electromagnetic radiation, whether visible light (e.g., having a wavelength of about 380-780 nm) or ultraviolet (UV) light (e.g., having a wavelength of about 190-320 nm (UV B light) or about 320-380 nm (UV A light)). Some containers also include the capacity to reduce exposure of the container's contents to infrared light, or a second component with such a capacity. The containers that may be used include those made from a polyolefin such as polyethylene, polypropylene, polyethylene terephthalate, polycarbonate, polymethylpentene, polybutene, or a combination thereof, especially polyethylene, polypropylene, or a combination thereof. In some embodiments, the container is a glass container. The container may further be disposed within a second container, for example, a paper, cardboard, paperboard, metallic film, or foil, or a combination thereof, container to further reduce exposure of the container's contents to UV, visible, or infrared light. Compounds and compositions benefiting from reduced discoloration, decomposition, or both during storage, include an ophthalmic pharmaceutical composition provided herein. An ophthalmic pharmaceutical composition provided herein may need storage lasting up to, or longer than, three months; in some cases up to, or longer than one year. The containers may be in any form suitable to contain the contents; for example, a bag, a bottle, or a box.

As explained herein, an aqueous ophthalmic composition or method of the present disclosure comprises, inter alia, WS-12, which modulates, and in particular is an agonist of Transient Receptor Potential cation channel subfamily M member 8, or TRPM8 receptor. The TRPM8 receptor is a protein that is coded by the TRPM8 gene in humans (Clapham D E, et al. 2005. Pharmacological Reviews 57 (4): 427-50). TRPM8 is an ion channel that, after activated, allows sodium ions ($Na^+$) and calcium ions ($Ca^{2+}$) to enter the cell, thus generating depolarization of said cell, leading to a change in the membrane potential. The TRPM8 protein is expressed in sensory neurons and is activated by cold temperatures (approximately below 26° C.), by chemical agents, and by voltage. TRPM8 is also expressed in the prostate, the lungs, and the bladder.

The human TRPM8 gene is located in chromosome 2 in the 2p37.1 region; and codes for a protein of 1104 amino acids (NP-076985.4) coded by the sequence of nucleotides NM-024080.4. The TRPM8 gene has six trans-membrane segments, with the C and N terminal ends on the cytoplasmic side. Four subunits tetramerise to form active channels.

The TRPM8 receptor is involved in the control of tear production and its activation using agonists thereof results in increased tear production. Specifically, cold thermoreceptors innervating the cornea in mammals keep tonic trigger activity at normal corneal temperature and are markedly sensitive to minor thermal variations in the eye surface, such as those resulting from evaporation of the precorneal tear film that occurs in the intervals between blinking and during exposure to dry environments. This marked cold sensitivity is the result of a high expression of TRPM8 channels that critically determine a spontaneous basal activity and an increase in the frequency of triggering in response to cold. Moreover, the removal of TRPM8 channels with genetic techniques halves tear secretion in mice. Partial silencing by corneal heating also reduces tear secretion in humans.

In light of the above, TRPM8 is a molecular target for the detection of moisture in cold thermoreceptor nerve fibers innervating the exposed eye surface in land animals.

In some embodiments, provided herein are methods of treating an ophthalmic disease or condition, the disease or condition involving tear production and/or reducing symptoms thereof comprising administering a therapeutically effective amount of a composition comprising a molecule binding specifically to the TRPM8 (Transient Receptor Potential Cation Channel subfamily M member 8) receptor to a subject in need thereof, wherein the binding of the molecule to the TRPM8 receptor modulates the activity of the TRPM8 channel;

wherein the binding of the molecule to the TRPM8 receptor increases or decreases tear secretion caused by ophthalmic disease or condition;

wherein the concentration of the molecule needed to bind and modulate the TRPM8 receptor in tissues is not sufficient to be cytotoxic to the subject in need thereof; and wherein the molecule is WS-12 or a salt thereof.

The words "treating" or "treatment" designate both therapeutic and prophylactic treatment or preventive measures, where the object is to prevent or stop (reduce) an unwanted physiological change or disorder, such as dryness of the eyes, vagina, or mouth. For the purpose of this disclosure, beneficial or wanted clinical outcomes include, without limitation, symptom relief, reduction of disease extent, stabilized pathological condition (specifically not worsened), delayed or stopped disease progression, improved or palliated pathological condition and remission (both partial and total), both detectable and non-detectable. Subjects needing treatment include subjects already suffering the disease or disorder, as well as those susceptible of suffering the disease or disorder or those for whom the disease or disorder should be prevented.

The "treatment method" is defined as the administration to a subject needing this treatment of pharmaceutical composition comprising a TRPM8 agonist, e.g. WS-12.

In the present disclosure, "TRPM8 receptor agonist" is defined as any molecule binding specifically to the TRPM8 receptor and that, upon binding, can cause an increase in the activity of the TRPM8 channel, i.e., that increases sodium and calcium flow through the channel causing a cell depolarization. These agonists increase the stimulation of tear secretion by cold-sensitive fibers. There is a great variety of studies available to detect the activity of TRPM8 receptor agonists, such as the whole-cell, patch-clamp electrophysiological tests mentioned in the examples of this disclosure (see example 1), the calcium microscopy methods (Bodding et al., 2007, Cell Calcium, 42, 618-628) and the methods based on the fluorometric imaging plate reader assay (Behrendt et al., 2004. J. Pharmacol. 141, 737-745), amongst others. As explained above, WS-12 is a TRPM8 receptor agonist, and produces a cooling sensation (via the TRPM8 receptor), which may reduce discomfort and pain.

In some embodiments, an ophthalmic pharmaceutical composition of the instant disclosure includes those listed in Table 2.

TABLE 2

| Component | Formulation Function | 1 Qty (% w/v) | 2 Qty (% w/v) | 3a Qty (% w/v) | 4a Qty (% w/v) |
| --- | --- | --- | --- | --- | --- |
| WS-12 | Active Ingredient | 0.003 | 0.0014 | 0.001519 | 0.00076 |
| Hypromellose | Viscosity Modifier | 0.14 | 0.14 | 0.45 | 0.45 |
| Polyoxyl 35 Castor Oil | Solubilizing Agent | 3.00 | 3.00 | 3.00 | 3.00 |
| Sodium Dihydrogen Phosphate Dihydrate | Buffer | 0.78 | 0.78 | 0.78 | 0.78 |
| Sodium Chloride | Tonicity Agent | 0.55 | 0.55 | 0.55 | 0.55 |
| Sodium Hydroxide | pH Adjuster | q.s. to pH 7 | q.s. to pH 7 | q.s. to pH 7 | q.s. to pH 7 |
| Purified Water | Solvent | q.s. | q.s. | q.s. | q.s. |

The present disclosure may be better understood by reference to the following non-limiting examples, which are provided as exemplary of the present disclosure. The following examples are presented in order to more fully illustrate the preferred embodiments of the present disclosure. They should in no way be construed, however, as limiting the broad scope of the present disclosure.

EXAMPLES

Preparation of Formulations of the Present Disclosure

In some embodiments, an ophthalmic pharmaceutical composition of the present disclosure comprises, among other ingredients, WS-12 and a solubilizer, particularly polyoxyl 35 castor oil (KOLLIPHOR EL). Polyoxyl 35 castor oil is a polyethoxylated form of castor oil formed from the reaction between castor oil and ethylene oxide. It is a non-ionic surfactant that is miscible with water. In some embodiments, an ophthalmic pharmaceutical composition of the present disclosure further comprises hypromellose (METHOCEL F4M), which increases the viscosity of the composition. Moreover, an ophthalmic pharmaceutical composition of the present disclosure is buffered to have a desired pH. In some embodiments, the desired pH is about 7, and the buffer used is phosphate buffer. Sodium chloride may also be included in order to make an ophthalmic pharmaceutical composition of the present disclosure isotonic.

As explained above, WS-12 is insoluble in water. Regardless, it was necessary to identify excipients that would provide WS-12 with a solubility of about 200 μM (0.0058%) in an aqueous medium compatible with administration (e.g., topical administration) to a human (e.g., a human eye). Several solubilizers were evaluated, including PEG 400 (polyethylene glycol 400), KOLLIDON 30 (polyvinylpyrrolidone), propylene glycol, TWEEN 80 (polyoxyethylene (20) sorbitan monooleate), KOLLIPHOR® EL or KOLLIPHOR® ELP (polyoxyl 35 castor oil) and tyloxapol (ethylene oxide-formaldehyde-p-octylphenol copolymer). It was determined that TWEEN 80 significantly increased WS-12 solubility. However, the concentration of TWEEN 80 required to provide this increase was greater than the highest previously used level of TWEEN 80 (i.e. 4%) in any heretofore marketed ophthalmic product, as indicated in FDA Inactive Ingredient Database. It was found that the excipients KOLLIDON® 30 (polyvinylpyrrolidone), propylene glycol, and tyloxapol (ethylene oxide-formaldehyde-p-octylphenol copolymer) failed to solubilize WS-12 to the desired level of 200 μM. KOLLIPHOR® EL concentrations of 3% w/v successfully dissolved WS-12 at levels of 200 μM, and polyoxyl 35 castor oil has been used in marketed ophthalmic products at a concentration of about 5% (FDA Inactive Ingredient Database). Hence, in a particular embodiment, an ophthalmic pharmaceutical composition provided herein comprises about 3% KOLLIPHOR® EL w/v as a solubilizer. The solubility was determined by adding an excess of WS-12 to a composition, agitating at the stated temperatures in Table 3 (about 2° C. to about 8° C., and about 17° C.) to allow the WS-12 to reach equilibrium solubility, filtering the mixture to remove undissolved WS-12, and determining by HPLC the amount of WS-12 dissolved in the composition.

TABLE 3

Solubility of WS-12 in an Ophthalmic Pharmaceutical Composition of the Present Disclosure.

| Formulation | WS-12 Solubility (mg/mL) 2°-8° C. | WS-12 Solubility (mg/mL) Room Temp (about 17° C.) |
| --- | --- | --- |
| 3% KOLLIPHOR EL 0.14% hypromellose 0.78% Na dihydrogen phosphate dihydrate 0.55% NaCl pH 7 | 0.041 | 0.055 | pH and osmolality are critical properties of an ophthalmic pharmaceutical composition for the topical ophthalmic route of topical administration to an eye. A pH of about 7 was selected to be close to pH of human tears for physiological comfort. A phosphate buffer was used to maintain pH 7. For comfort during administration, NaCl was added to make a given formulation isotonic with a similar osmolality to human tears (about 300 mOsm/kg).

As described herein, an ophthalmic pharmaceutical composition of the present disclosure further comprises a viscosity modifier. In some embodiments, an ophthalmic pharmaceutical composition provided herein is more viscous than water, with a viscosity greater than 1.0 cP. Thus, an ophthalmic pharmaceutical composition of the instant disclosure can have a viscosity of about 2 cP, about 3 cP, or about 4 cP, or even greater. In some embodiments, an ophthalmic pharmaceutical composition of the instant disclosure has a viscosity of less than about 5 cP or less than about 4 cP, e.g., about 3 cP.

Physicochemical and Biological Properties of an Ophthalmic Pharmaceutical Composition of the Disclosure Solubility: Concentrations of WS-12 for study described infra (0.0014% and 0.003% w/v) are below saturation limit of WS-12. Thus, precipitation is not a concern.

Particulate Matter: Particulate matter is controlled as part of the drug product specification, and the controls are consistent with compendia! methods.

Osmolality: An ophthalmic pharmaceutical composition of the present disclosure may have an osmolality ranging from about 270 to about 340 mOsm/kg. In a particular embodiment, the osmolality is about 300 mOsm/kg. Sodium chloride is used as the osmotic adjusting agent.

Study

Study Background: The study disclosed herein examines the efficacy of an ophthalmic pharmaceutical composition of the instant disclosing comprising TRPM8 agonist WS-12 to treat, ameliorate or prevent dry eye, as well as signs or symptoms associated therewith.

The TRPM8 (Transient Receptor Potential Melastatin) receptors are cold-sensitive thermoreceptors that play an important role in tear film homeostasis (Eguchi et al., Biomed. Res. Int. 2017; Craig et al., The Ocular Surface 2017, 15, 276-283). These receptors are located on the eyelid and cornea and detect drops in corneal temperature associated with tear evaporation on the ocular surface.

A large (n=369) multicenter, vehicle-controlled, double masked, randomized Phase 2b study was conducted to evaluate the safety and efficacy of two ophthalmic pharmaceutical compositions of the instant disclosure wherein one had a WS-12 concentration of 0.0014% w/v and the other a WS-12 concentration of 0.003% w/v. Criteria for Inclusion of a Subject into the Study:

a. Male or female, 30 years of age or older at the screening visit
  b. Has a history of dry eye disease within the previous 6 months
  c. Has used, and/or desired using artificial tears for dry eye disease within 2 months prior to the screening visit.
  d. Symptoms of dry eye disease based on Ocular Discomfort Score (ODS)-VAS and Global SANDE questionnaires at both the Screening and Baseline visits
  e. Anesthetized Schirmer test score≥2 and <10 mm/5 min at both Screening and Baseline visits.
  f. Total corneal fluorescein staining score of ≥2 and ≤15 based on modified NEI grading scheme (0-20), with no one region scoring >3 at screening visit.
  g. BCVA of 20/200 (0.70 logMar) or better in both eyes at both the Screening and Baseline visits.
  h. Good general and ocular health, as determined by investigator using medical history, ophthalmic examination, blood chemistry and hematology, urinalysis, and vital signs at the Screening visit.
  i. Capable of giving signed informed consent, which includes compliance with the requirements and restrictions listed in the informed consent form (ICF) and in this protocol.
  j. Able, as assessed by the investigator, and willing to follow study instructions and likely to complete all required study visits.

Thus, in some embodiments of the methods provided herein, the subject comprises one or more of the above-identified criteria for inclusion.

Criteria for Exclusion of a Subject into the Study: History or presence of any ocular disease or disorder (other than DED) in either eye that would, in the opinion of the investigator, likely interfere with the interpretation of the study results or subject safety.

a. History of ocular surgery within one (1) year prior to the Screening visit.
  b. Punctal or intracanalicular plug present in either eyelid within 1 year prior to the Screening visit or anticipated plug insertion or occlusion at any time during the study.
  c. Use of contact lenses in either eye within seven (7) days prior to screening visit or planned use during the study.
  d. Regular use of lid hygiene within 14 days prior to the Screening visit or any planned use during study.
  e. Use of any topical ocular medications for DED, ocular corticosteroid or NSAID, glaucoma medications, eye whitening, topical antibiotics, topical antihistamines, mast cell stabilizers or other OTC or nutritional supplements with exception of artificial tears within thirty (30) days prior to Screening visit or anticipated use during study.
  f. Use of systemic corticosteroids started <90 days prior to Baseline visit or change in dose during study. Non-ocular topically applied corticosteroids (including nasal inhalers) will be permitted.
  g. Known allergies or sensitivity to the study interventions or study diagnostic agents.
  h. Positive pregnancy test at Screening or Baseline visits, currently breastfeeding or plans to become pregnant during the study. Women of childbearing potential not using a medically acceptable form of birth control.
  i. Subject has a condition or is in a situation, in the investigator's opinion, may put the subject at significant risk or may confound the study results.

Thus, in some embodiments of the methods provided herein, the subject does not have one or more of the above-identified criteria for exclusion.

Subject Disposition: A total of 369 subjects were selected and randomized. The majority of the subjects (>94% of active treatment groups) completed the study to Day 84.

TABLE 4

Breakdown of Subjects Based Upon Formulation Administered and Discontinuation of Study.

|  | 0.0014% WS-12 Formulation w/v n = 121 | 0.003% WS-12 formulation w/v n = 122 | Vehicle N = 126 |
|---|---|---|---|
| Number of Subjects Randomized | 121 | 122 | 126 |
| Number of Subjects that completed study (%) | 114 (94.2%) | 115 (94.3%) | 116 (92.1%) |
| Number of Subjects that Discontinued Study (%) and Cause: | | | |
| Adverse Event | 3 (2.5%) | 2 (1.6%) | 2 (1.6%) |
| Withdrawal of Consent | 4 (3.3%) | 3 (2.5%) | 2 (2.4%) |
| Non-Compliant | 0 | 1 (0.8%) | 1 (0.8%) |
| Lost to Follow-up | 0 | 0 | 1 (0.8%) |
| Investigator Decision | 0 | 0 | 1 (0.8%) |
| Protocol Violation | 0 | 1 (0.8%) | 2 (1.6%) |

The adverse events leading to discontinuation included:
  (a) installation site burning (2 administered WS-12 0.0014% w/v formulation and 1 administered WS-12 0.003% w/v formulation;
  (b) installation site stinging (1 administered WS-12 0.003% w/v formulation);
  (c) eyelid edema (1 administered WS-12 0.0014% w/v formulation;
  (d) epithelial defect (1 in vehicle); and
  (e) respiratory failure (1 in vehicle).

TABLE 5

Baseline Demographic of Subjects of the Study.

|  | 0.0014% WS-12 (Formulation 2) n = 121 | 0.003% WS-12 (Formulation 1) n = 122 | Vehicle N = 126 |
|---|---|---|---|
| Age (Years) | | | |
| Mean (SD) | 65.5 (10.89) | 62.6 (13.01) | 63.1 (11.90) |
| Range | 31-85 | 30-87 | 30-90 |
| Gender | | | |
| Female, Number (%) | 82 (67.8%) | 92 (75.4%) | 92 (73.0%) |
| Race, Number (%) | | | |
| White/Caucasian | 97 (80.2%) | 92 (75.4%) | 99 (78.6%) |
| Black/African America | 15 (12.4%) | 18 (14.8%) | 18 (14.3%) |
| Asian | 8 (6.6%) | 11 (9.0%) | 7 (5.6%) |
| Other | 1 (0.8%) | 1 (0.8%) | 2 (1.6%)) |

Description of Study: The study performed with respect to an ophthalmic pharmaceutical composition of the present disclosure was a multicenter, vehicle-controlled, double-masked, randomized study. All subjects enrolled suffered from dry eye disease. The study consisted of Screening and Baseline visits to determine eligibility followed by efficacy assessments at Day 14 (Visit 3), 28 (Visit 4) and 84 (Visit 5/Study Exit). Safety was assessed at all study visits. All subjects were exposed to the Controlled Adverse Environment (CAE) endpoints at the Screening, Baseline, Day 28 and Day 84 visits. Only subjects who qualified based on inclusion/exclusion criteria were enrolled and randomized at a 1:1:1 ratio within each site, to receive placebo (e.g., Formulation 1 without WS-12), WS-12 0.0014% or WS-12 0.003% administered as 1 drop in each eye twice daily for 84 days. The objective of the study was to evaluate the safety, tolerability and efficacy of administration a topical ophthalmic pharmaceutical composition of the present disclosure compared to a vehicle administered twice daily in subjects with dry eye disease. The timeline for the study is forth below in Table 6.

TABLE 6

| Visit 1 (Day −14) | Vehicle Run-In Period (OU Dosing BID WS-12 Vehicle) | | |
|---|---|---|---|
| Visit 2 Baseline Day 1 | 0.0014 % WS-12 (Formulation 2) (n = 120) | 0.003 % WS-12 (Formulation 1) (n = 120) | Vehicle (n = 120) (OU Dosing BID) |
| Visit 3 (Day 14) | (OU Dosing BID) | (OU Dosing BID) | |
| Visit 4 (Day 28) | | | |
| Visit 5 (Day 84) | | | |

Effect of Ophthalmic Pharmaceutical Composition of the present disclosure on Symptoms of Dry Eye Disease: Table 7 below sets forth the effect of the administration of an ophthalmic pharmaceutical composition to subjects pursuant to the description of the study discussed above on the following symptoms associated with dry eye disease:
 (a) ocular discomfort Score (ODS-VAS);
 (b) SANDE score;
 (c) eye dryness (EDS-VAS).

TABLE 7

| SYMPTOM | TIMING |
|---|---|
| Ocular Discomfort Score (ODS-VAS) | |
| Change from Baseline ODS-VAS | Day 84 (p = 0.028) |
| Mean ODS-VAS | Day 84 (p = 0.039) |
| SANDE | |
| Change from Baseline SANDE | Day 14 (p = 0.025); Day 28 (p = 0.0005); Day 84 (p = 0.002) |
| Mean SANDE | Day 28 (p = 0.017); Day 84 (p = 0.008) |
| % Responders SANDE (≥20) | Day 28 (p = 0.0004); Day 84 (p = 0.0497) |
| % Responders SANDE (≥30) | Day 28 (p = 0.0231); Day 84 (p = 0.0007) |
| % Responders SANDE (≥40) | Day 28 (p = 0.0085); Day 84 (p = 0.0025) |
| Eye Dryness (EDS-VAS) | |
| Change from Baseline-EDS-VAS | Day 84 (p = 0.03) |
| Mean EDS-VAS | Day 84 (p = 0.075) |
| Change from Baseline EDS-VAS (Post CAE) | Day 84 (p = 0.009) |

The results of the study demonstrated improvements in symptoms of dry eye disease with administration of a therapeutically effective amount of an ophthalmic pharmaceutical composition of the present disclosure.

FIG. 1 clearly demonstrates that at Day 84 of treatment, the subjects reported a change in ocular discomfort as compared to that reported at their respective Baseline visits of −20.6 for the 0.003% w/v WS-12 ophthalmic pharmaceutical composition of the present disclosure and compared to a −13.36 decrease reported for the vehicle BID reported for the same time period. It should be noted that a decrease in a score represents an improvement, e.g., a reduction of the symptom.

Figure 2:
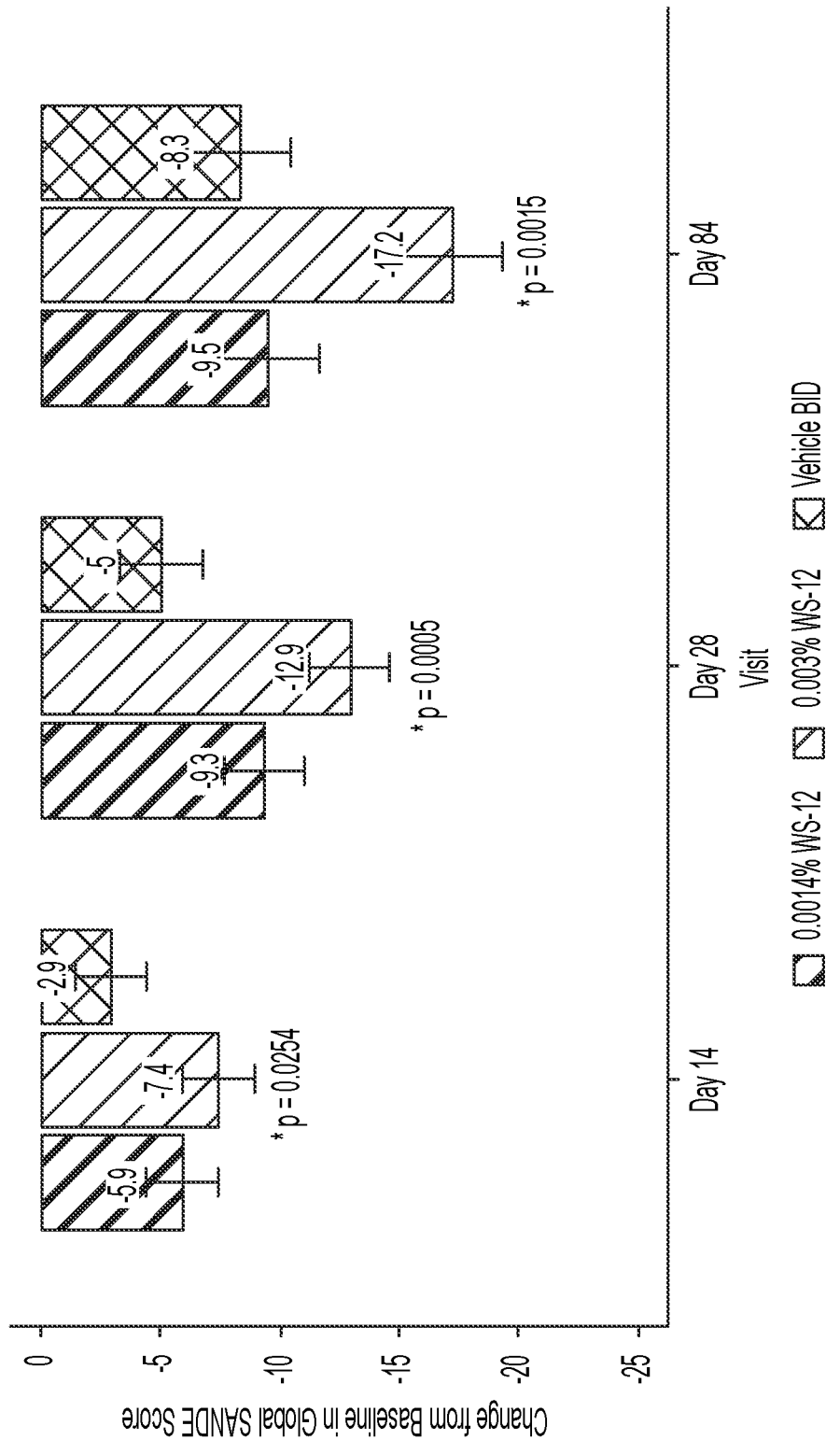
FIG. 2 is a bar graph setting forth the changes in SANDE score observed in subjects administered ophthalmic pharmaceutical composition of the instant disclosure.

FIG. 2 clearly demonstrates that the Global SANDE score for subjects administered the 0.003% w/v or the 0.0014% w/v WS-12 ophthalmic pharmaceutical compositions of the present disclosure for 84 days showed a decrease of 17.2 and 12.9, respectively, compared to scores obtained from the subjects at the Baseline Visit, which naturally occurred before for an ophthalmic pharmaceutical composition of the present disclosure was administered to the subjects.

Figure 3:
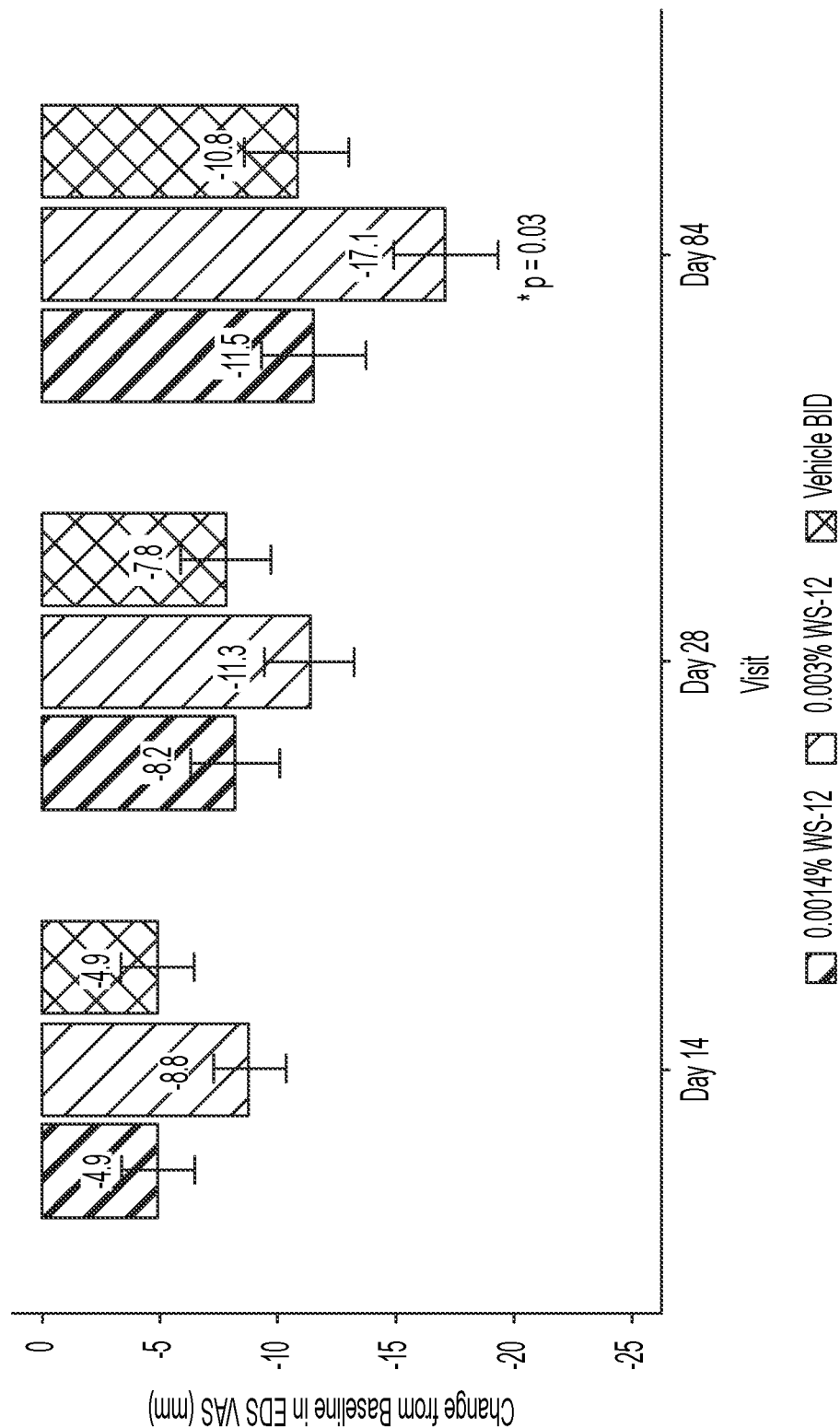
FIG. 3 is a bar graph setting forth the changes in the dry eye disease symptom VAS scores eye dryness (EDS-VAS) observed in subjects administered an ophthalmic pharmaceutical composition of the instant disclosure as compared to eye dryness observed before such administration.

FIG. 3 is a bar graph setting forth the changes in the Eye Dryness Symptom VAS scores (EDS-VAS) observed in subjects administered an ophthalmic pharmaceutical composition of the instant disclosure as compared to eye dryness observed before such administration. FIG. 3 clearly demonstrates that the eye dryness subjects reported after administration of the 0.003% w/v WS-12 ophthalmic pharmaceutical composition of the present disclosure decreased 17.1 as compared to eye dryness the subjects reported at their respective Baseline visits, which subjects receiving only the vehicle reported only a 10.8 decrease in eye dryness for the same time period.

Effect of Ophthalmic Pharmaceutical Composition of the present disclosure on Signs of Dry Eye Disease: As explained above, signs of dry eye disease evaluated in the study disclosed herein were:
 (a) Schirmer Score (unanesthetized);
 (b) Conjunctival Redness; and
 (c) Total Ocular Surface Staining.

TABLE 8

| SIGN | TIMING |
|---|---|
| Schirmer Score (Unanesthetized)* | |
| Change observed from Baseline Visits *measured only at Baseline visit and Day 14 | Day 1 (p < 0.0001), Day 14 (p < 0.0001) |
| Conjunctival Redness | |
| Change from Baseline Conjunctival Redness | Day 84 (p = 0.022) |
| Ocular Surface Staining | |
| Change from Baseline Total Surface Staining | Day 14 (p = 0.012), Day 84 (p = 0.037) |
| Change from Baseline Conjunctival Staining | Day 14 (p = 0.005) |
| Mean Conjunctival Staining | Day 14 (p = 0.054) |

Figure 4:
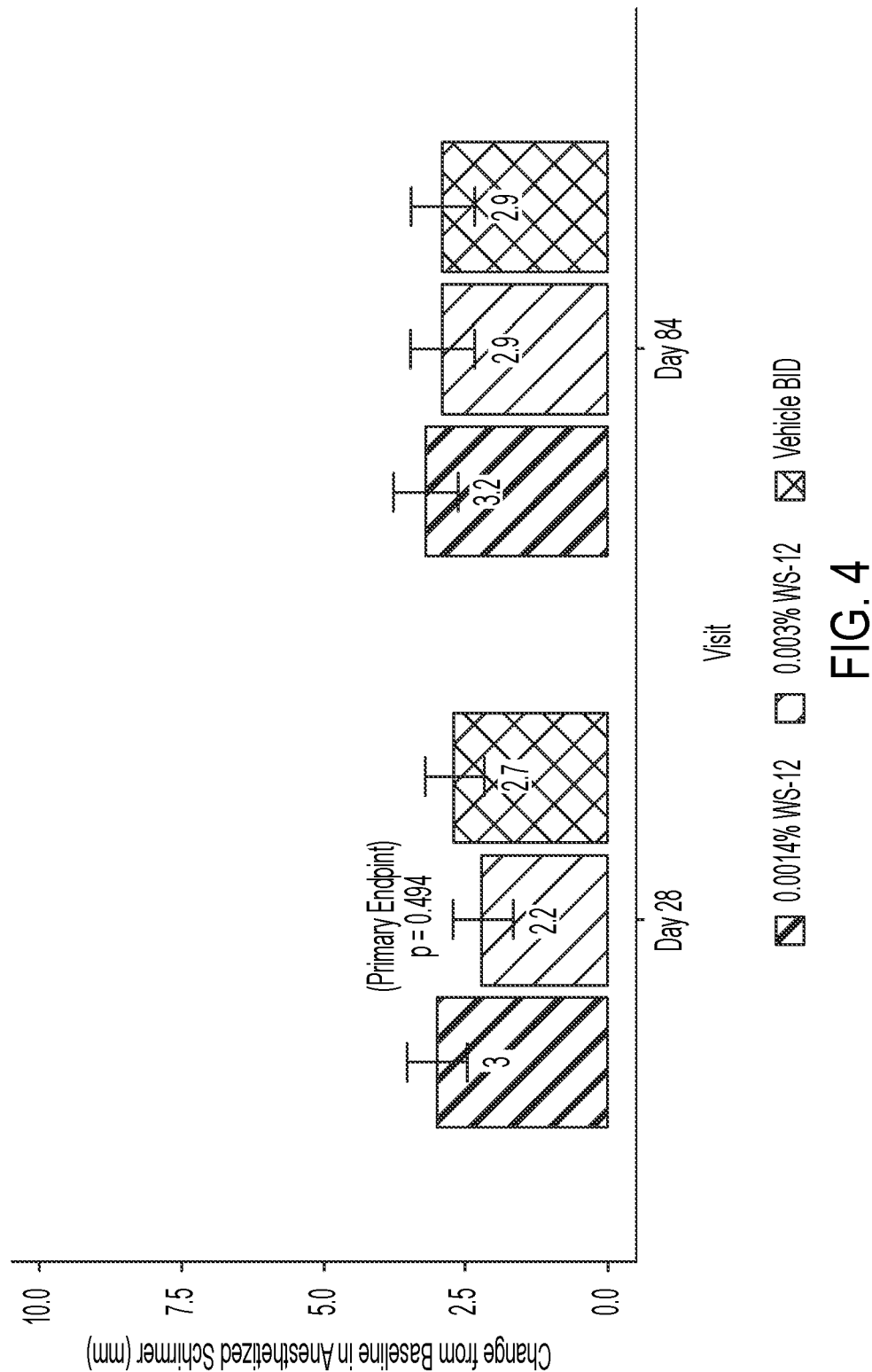
FIG. 4 is a bar graph comparing changes in Schirmer score for anesthetized subjects observed between scores obtained at the Baseline visit and scores obtained from subjects at Day 28 and Day 84 of the study described herein with treatment with either an 0.0014% w/v or 0.003% w/v WS-12 ophthalmic pharmaceutical composition as disclosed herein.
Figure 5:
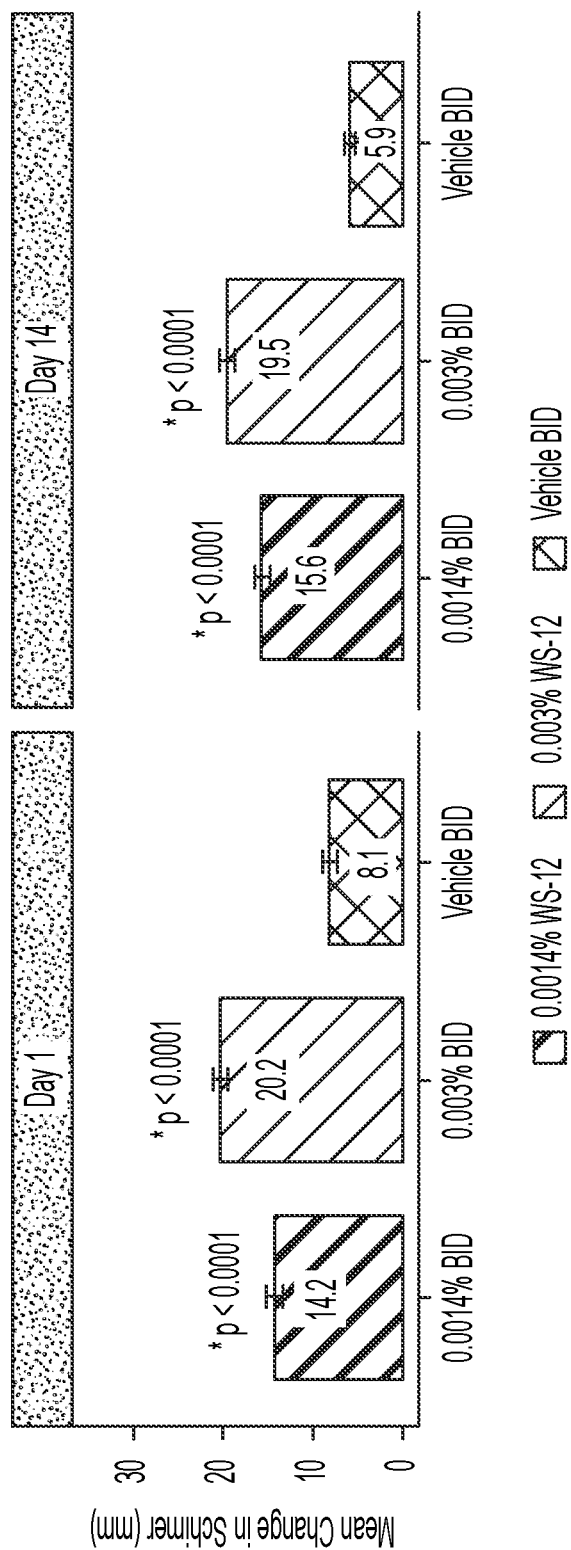
FIG. 5 is a bar graph comparing changes in Schirmer score for unanesthetized subjects observed between scores obtained at the Baseline visit and scores obtained from subjects at Day 1 and Day 14 of the study described herein with treatment with either an 0.0014% w/v or 0.003% w/v WS-12 ophthalmic pharmaceutical composition as disclosed herein.

Unanesthetized Schirmer Score: The data of FIG. 4 clearly shows that treatment with either an 0.0014% w/v or 0.003% w/v WS-12 ophthalmic pharmaceutical composition as disclosed herein resulted in an increased Schirmer score, which means tear production for the subjects increased with respect to the scores of those who were administered the vehicle only. FIG. 5, further confirms this observation. FIG. 5 demonstrates a statistically significant number of subjects administered an ophthalmic pharmaceutical composition achieved the endpoint of an increase of ≥10 mm on the Schirmer score compared with those to whom the vehicle only was administered.

Figure 6:
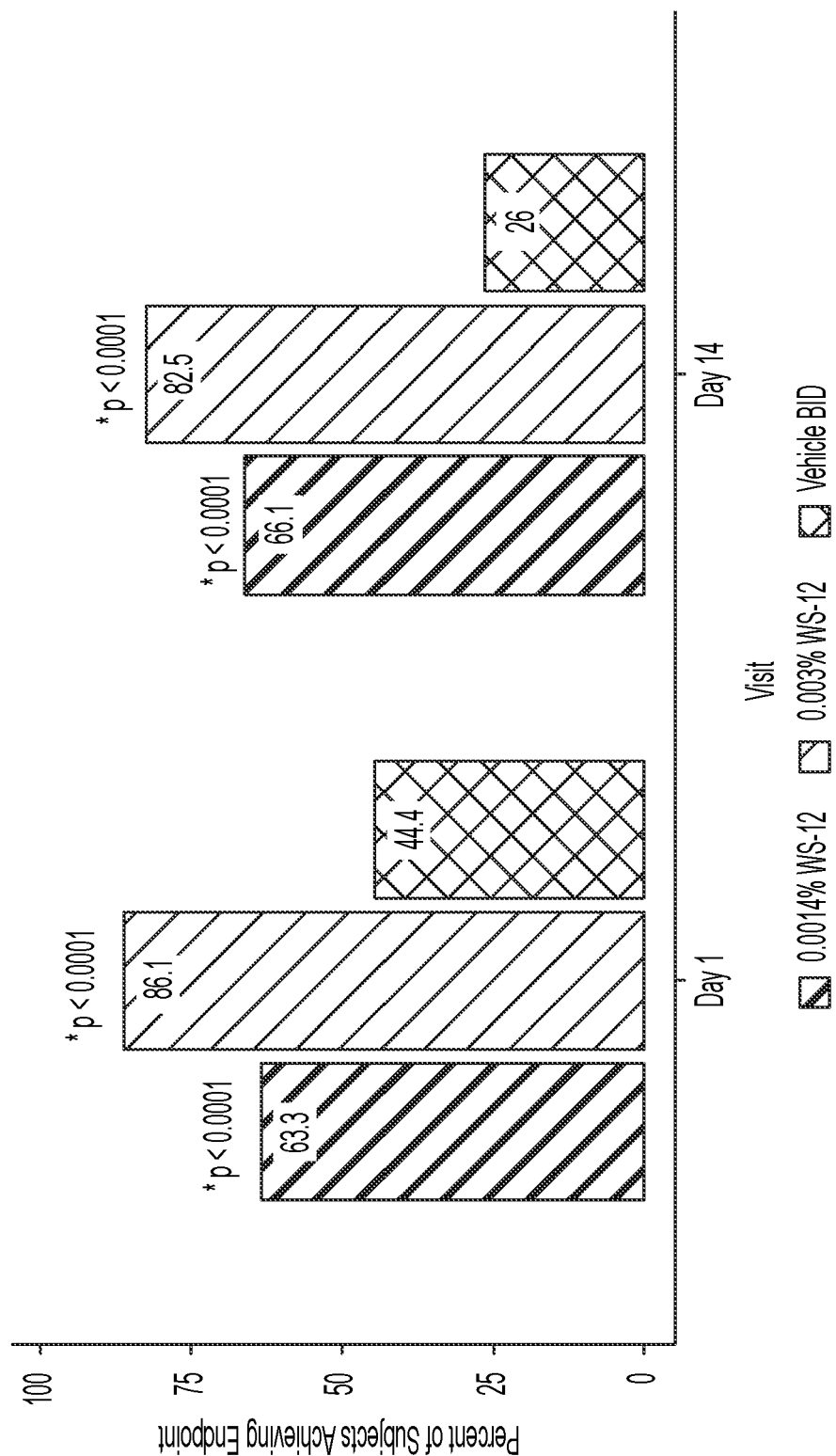
FIG. 6 is a bar graph that tracks the conjunctival Redness for subjects of the study to whom the 0.0014% w/v WS-12 and 0.003% w/v WS-12 ophthalmic pharmaceutical compositions of the present disclosure were administered.

Conjunctival Redness: it is well established that those suffering from dry eye disease may suffer from conjunctival redness, Conjunctival redness was graded according to the following scale (Half (0.5) unit increments may be used): None 0=Normal, without vasodilation; Trace 1=Trace ciliary or conjunctival vasodilation; Mild 2 Broad ciliary vasodilation; Moderate 3=Broad ciliary and slight, horizontal conjunctival vasodilation; Severe 4=Broad ciliary. Measurements were taken on the Baseline visit and days 14, 28 and 84 of the study. FIG. 6 clearly shows that subjects to whom the 0.003% w/v WS-12 ophthalmic pharmaceutical composition of the present disclosure demonstrated a decline in conjunctival redness as compared to those subjects to whom only the vehicle was administered.

Figure 7:
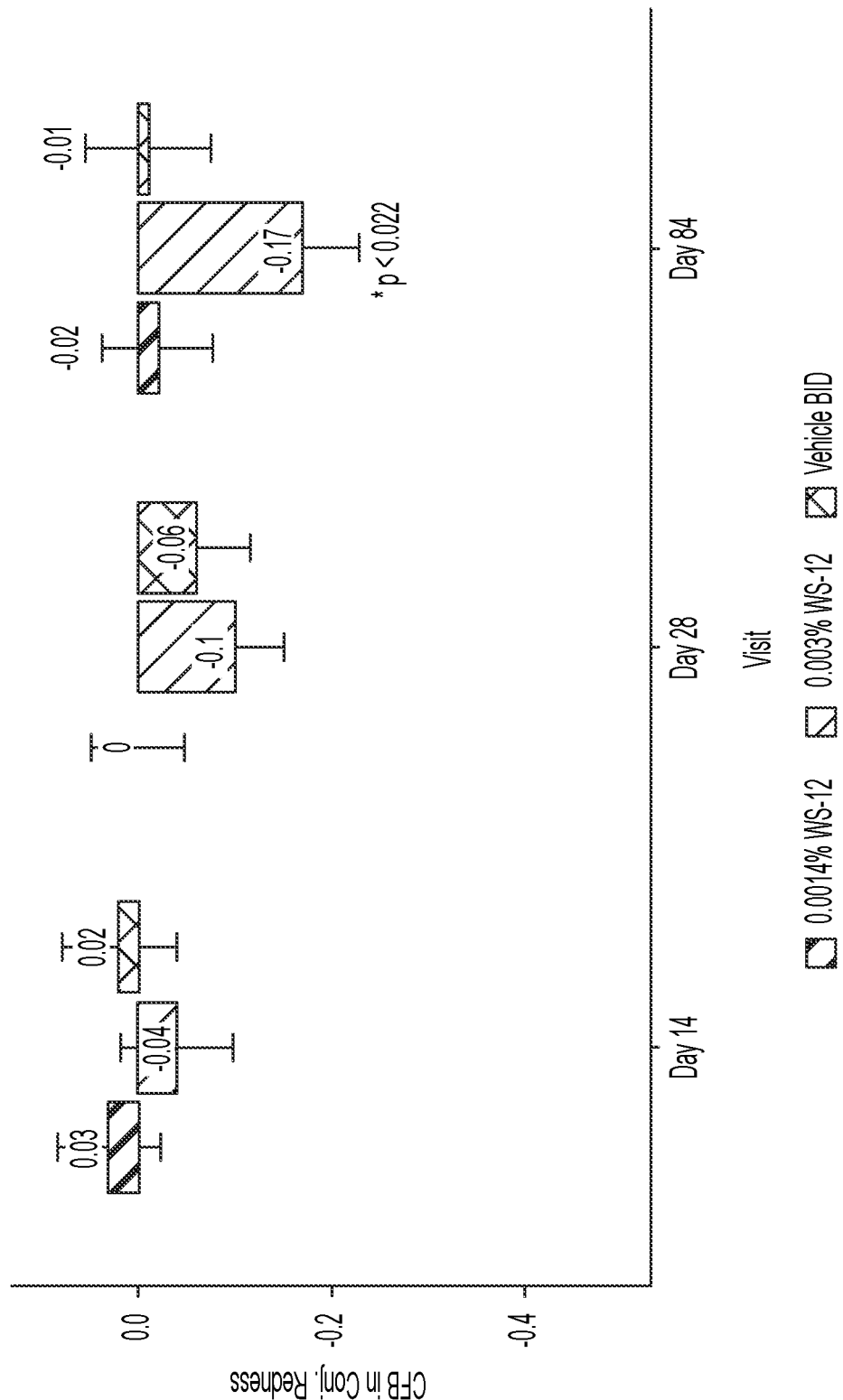
FIG. 7 is a bar graph of subjects for whom ocular surface staining was performed on days 14, 28 and 84 of the study.

Ocular Surface Staining: Ocular surface staining is a method for observing ocular surface damage. The data presented in FIG. 7 clearly show that administration of an ophthalmic pharmaceutical composition of the present disclosure to subjects resulted in a decrease in ocular surface damage, while those subjects of the study to whom only the vehicle was administered exhibited little to no improvement to an actual worsening in surface damage.

Overall Safety of an Ophthalmic Pharmaceutical Composition of the Disclosure: Overall, a pharmaceutical ophthalmic composition of the present disclosure is well-tolerated. No serious Treatment-Emergent Adverse Events (TEAEs) were considered related to an ophthalmic pharmaceutical composition of the present disclosure. Moreover, few TEAEs led to study discontinuation and most were ocular in nature. Table 9 is a summary regarding overall safety

TABLE 9

|  | 0.0014% w/v WS-12 (Formulation 2) n-121 | 0.003% w/v WS-12 (Formulation 1) n-122 | Vehicle n = 126 |
|---|---|---|---|
| Any TEAEs | 57 (47.1%) | 63 (51.6%) | 26 (20.6%) |
| Serious TEAEs | 1 (0.8%) | 1 (0.8%) | 2 (1.6%) |
| Serious TEAEs related to Oph. Pharm. Comp. of Disclosure | 0 | 0 | 0 |
| TEAEs by Severity |  |  |  |
| Mild | 50 (41.3%) | 59 (48.4%) | 18 (14.3%) |
| Moderate | 5 (4.1%) | 3 (2.5%) | 7 (5.6%) |
| Severe | 2 (1.7%) | 1 (0.8%) | 1 (0.8%) |
| TEAEs Leading to Discontinuation | 3 (2.5%) | 2 (1.6%) | 4 (3.2%) |

Ocular Treatment-Emergent Adverse Events: As explained above, most of the TEAEs were ocular in nature. Table 10 is a breakdown of the types of ocular TEAEs observed, and their respective frequencies.

TABLE 10

|  | 0.0014% w/v WS-12 Pharm. Comp. of disclosure n-121 | 0.003% w/v WS-12 Pharm. Comp. of disclosure n-122 | Vehicle n = 126 |
|---|---|---|---|
| Any Ocular TEAE | 51 (42.1%) | 59 (48.4%) | 13 (10.3%) |
| Eye Disorder |  |  |  |
| Chalazion | 12 (9.9%) | 6 (4.9%) | 9 (7.1%) |
| Conjunctival hemorrhage | 0 | 0 | 1 (0.8%) |
| Conjunctival hyperemia | 0 | 0 | 1 (0.8%) |
| Conjunctival edema | 1 (0.8%) | 0 | 0 |

TABLE 10-continued

|  | 0.0014% w/v WS-12 Pharm. Comp. of disclosure n-121 | 0.003% w/v WS-12 Pharm. Comp. of disclosure n-122 | Vehicle n = 126 |
|---|---|---|---|
| Corneal epithelium defect | 1 (0.8%) | 0 | 0 |
| Corneal infiltrate | 0 | 0 | 1 (0.8%) |
| Eye irritation | 1 (0.8%) | 0 | 0 |
| Eye pain | 1 (0.8%) | 0 | 0 |
| Eye pruritis | 1 (0.8%) | 0 | 0 |
| Eyelid margin crusting | 1 (0.8%) | 0 | 0 |
| Eyelid edema | 0 | 0 | 1 (0.8%) |
| Lacrimation increased | 1 (0.8%) | 0 | 0 |
| Photophobia | 2 (1.7%) | 0 | 0 |
| Posterior capsular opacification | 1 (0.8%) | 0 | 0 |
|  | 0 | 0 | 1 (0.8%) |
| Retinal tear | 1 (0.8%) | 0 | 0 |
| Swelling of eyelid | 0 | 2 (1.6%) | 0 |
| Vision blurred | 0 | 1 (0.8%) | 1 (0.8%) |
| Visual acuity reduced | 2 (1.7%) | 2 (1.6%) | 2 (1.6%) |
| Visual impairment | 0 | 1 (0.8%) | 0 |
| Vitreous detachment | 2 (1.7%) | 0 | 1 (0.8%) |
| General Disorder and Admin. Site | 45 (37.2%) | 53 (43.4%) | 4 (3.2%) |
| Instillation site irritation | 1 (0.8%) | 0 | 0 |
| Instillation site burning or stinging | 45 (37.2%) | 53 (43.4%) | 4 (3.2%) |
| Instillation site pruritis | 1 (0.8%) | 1 (0.8%) | 0 |
| Infections |  |  |  |
| Conjunctivitis | 0 | 0 | 1 (0.8%) |
| Injury |  |  |  |
| Corneal Abrasion | 0 | 1 (0.8%) | 0 |
| Nervous System Disorders |  |  |  |
| Migraine with aura | 0 | 1 (0.8%) | 0 |
| Skin Manifestations |  |  |  |
| Echymosis | 1 (0.8%) | 0 | 0 |

Non-Ocular Treatment-Emergent Adverse Effects: As explained above, the majority of TEAEs were ocular related. Some though were non-ocular related. The non-ocular related TEAEs are listed in Table 11, as well as their respective frequencies of occurrence. A similar percentage of non-ocular treatment-emergent adverse events across all groups without notable findings. Also, none of the systemic adverse events were considered likely related or related to an ophthalmic pharmaceutical composition of the present disclosure.

TABLE 11

|  | 0.0014% w/v WS-12 pharm. Comp. of disclosure n-121 | 0.003% w/v WS-12 Pharm. Comp. of disclosure n-122 | Vehicle n = 126 |
|---|---|---|---|
| Any Ocular TEAE | 18 (14.9%) | 9 (7.4%) | 16 (12.7%) |
| Non-Ocular TEAE severity |  |  |  |
| Mild | 13 (10.7%) | 8 (6.6%) | 9 (7.1%) |
| Moderate | 4 (3.3%) | 1 (0.8%) | 6 (4.8%) |
| Severe | 1 (0.8%) | 0 | 1 (0.8%) |
| Non-ocular TEAs leading to discontinuation | 0 | 0 | 3 (2.4%) |

Summary: In this study, 369 dry eye subjects were randomized to one of 3 treatments:
(a) a 0.0014% w/v WS-12 ophthalmic pharmaceutical composition of the present disclosure (Formulation 2);

(b) a 0.003% w/v WS-12 ophthalmic pharmaceutical composition of the present disclosure (Formulation 1); and (c) a vehicle (Formulation 1 or 2 without WS-12).

The data obtained demonstrate that a statistically significant efficacy was demonstrated across multiple pre-specified symptom and sign endpoints with an ophthalmic pharmaceutical composition of the present disclosure, particularly with a 0.003% w/v WS-12 ophthalmic pharmaceutical composition of the present disclosure. Symptoms of a dry eye disease or disorder for which a statistically significant efficacy was demonstrated are:

(a) ocular discomfort;

(b) SANDE; and (c) Eye Dryness.

Signs of a dry eye disease or disorder for which a statistically significant efficacy for which a statistically significant efficacy was demonstrated are:

(a) tear production;

(b) conjunctival redness; and (c) ocular surface staining.

It was further observed that efficacy of an ophthalmic pharmaceutical composition of the present disclosure was observed within 14 days of the commencement of the study, and continued improvement of symptoms and signs of dry eye was demonstrated over the 3-month duration of the study. Sign efficacy was demonstrated as early as after the first dose (day 1). Sign and symptom efficacy was demonstrated on day 14.

Moreover, data obtained from the study demonstrated that an ophthalmic pharmaceutical composition of the present disclosure is safe, well tolerated, and the majority (approximately 95%) of all ocular adverse events were rated as mild, and less than 2% of the subjects being administered the 0.003% w/v WS-12 ophthalmic pharmaceutical composition of the present disclosure discontinued participation in the study due to adverse events. In addition, no systemic or serious adverse events were attributed to an ophthalmic pharmaceutical composition of the present disclosure.

Storage of an Ophthalmic Pharmaceutical Composition of the Disclosure

The ophthalmic pharmaceutical compositions of the present disclosure can be stored in unit dose or multidose containers made of a polymer, including one or more polyolefins. In some embodiments, the multidose container includes those having a design useful for multidose preservative free (MDPF) applications. WS-12 is a chemically stable molecule that is generally not susceptible to degradation by typical drug stressors (e.g., acid, base, peroxide, heat, light). WS-12, in the ophthalmic composition of the present disclosure, is physically unstable because it interacts with the polyolefin container that it is held in. The sorption processes decrease the effective concentration of WS-12 in the eye drop.

It was discovered that there is an inverse relationship between the crystallinity of the polyolefin and the amount of WS-12 absorbed into the polyolefin when the pharmaceutical composition is stored in contact with the polyolefin at elevated temperatures (e.g. 40° C.). Crystallinity was measured by determining the melting temperature of the polyolefin by DSC, with higher melting temperatures denoting greater crystallinity. Table 12 shows that polyolefins with high melting points, such as HDPE and PP, yielded the lowest percent loss in WS-12, while polyolefins with low melting points, such as LDPE 5, showed the greatest loss of WS-12.

TABLE 12

Melting temperatures of various polyolefins correlated with the percent loss of WS-12 concentration stored in the polyolefin container.

| Polyolefin Container Material | Melting Peak Temperature of Polyolefin by DSC (° C.) | Density of Polyolefin (g/cm³) | Percent Loss in WS-12 Concentration After Storage in Polyolefin Container for 2 Weeks at 40° C. |
|---|---|---|---|
| High Density Polyethylene (HDPE) | 127.4 | 0.950 | 1.3 |
| Polypropylene (PP) | 149.1 | 0.902 | 1.3 |
| Low Density Polyethylene (LDPE 1) | 118.2 | 0.933 | 2.8 |
| Low Density Polyethylene (LDPE 2) | 116.0 | 0.930 | 2.8 |
| Low Density Polyethylene (LDPE 3) | 114.4 | 0.928 | 3.3 |
| Low Density Polyethylene (LDPE 4) | 113.1 | 0.927 | 4.0 |
| Low Density Polyethylene (LDPE 5) | 107.8 | 0.919 | 4.5 |

LDPE 1, LDPE 2, LDPE 3, LDPE 4, and LDPE 5 in Table 12 correspond to LDPEs from different suppliers. Melting point values of the polyolefins were experimentally determined by differential scanning calorimetry (DSC). The densities of the polyolefins were as provided by the manufacturer's product data sheet.

Unit dose containers for the ophthalmic composition may be produced using blow-fill-seal (BFS) technology. This technology involves a continuous operation where the containers are formed, filled with product, and sealed. The unit dose containers are small and typically flexible to enable patients to squeeze the eye drop out with ease. Low density polyethylene (LDPE) is one commonly used polyolefin in BFS as containers made from it are generally manually pliable. The sorption of WS-12 by LDPE was found to be temperature dependent, with higher temperatures leading to greater losses of WS-12 out of solution and onto or into the container material by adsorption, absorbance, or both. For this reason, LDPE BFS containers holding the ophthalmic composition must be stored at 5° C. to minimize the loss of WS-12 out of solution to the container.

The 'curing' technique, or process, described herein exploits the temperature dependence of WS-12 absorption into LDPE to yield a product that is stable when stored at 25° C. In some embodiments, the curing technique includes the following steps: (a) producing the BFS containers filled with an ophthalmic pharmaceutical composition provided herein; (b) storing the filled BFS containers at a first temperature (e.g. 40° C.) to drive WS-12 into the LDPE container with the aim of saturating the container walls with WS-12; and (c) subsequently storing the BFS containers at a second temperature (e.g., 25° C.) whereupon further loss of WS-12 to the container walls is stemmed due to the above described saturation process.

Figure 8:
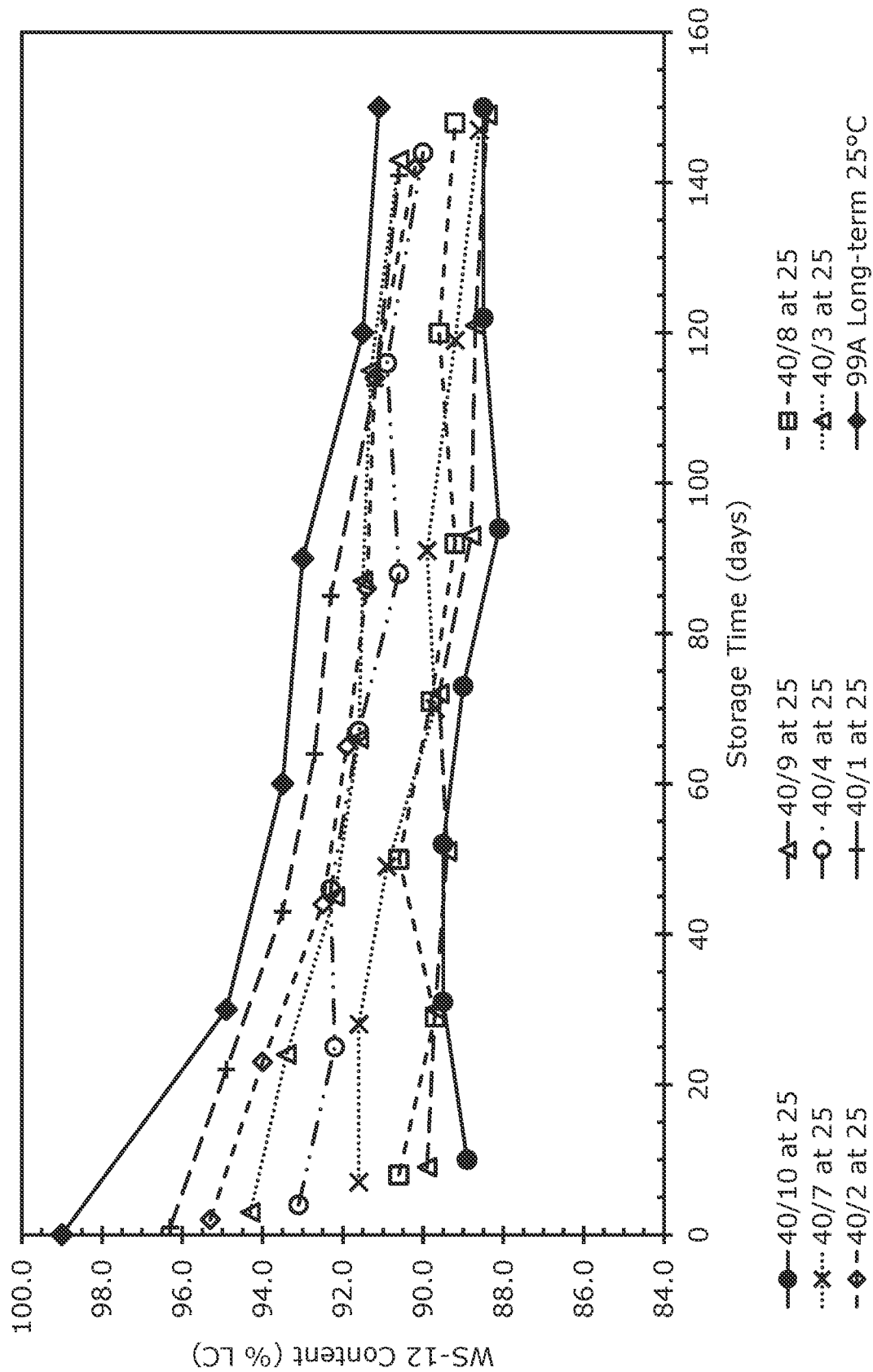
FIG. 8 shows WS-12 content over time in blow-fill-sealed containers including Formulation 1 after two-step storage conditions including a first storage temperature and a subsequent second storage temperature. Examples correspond to storage at 40° C. for 1, 2, 3, 4, 7, 8, 9, or 10 days followed by storage at 25° C. for up to about 150 days. A control sample was stored at 25° C. without first storing at 40° C.

FIG. 8 shows the trend of WS-12 content in BFS units that were produced and cured at 40° C. for 1, 2, 3, 4, 7, 8, 9, and 10 days, and subsequently stored at 25° C. for long term storage. The loss in WS-12 in the cured units is compared to units that did not undergo curing, i.e. they were only stored at 25° C. (99A long-term 25° C. trace). The first data point of each line represents the content of WS-12 in the BFS article after the curing period (e.g., the first temperature of storage). The amount of WS-12 lost to the LDPE increased as the duration of curing at 40° C. was increased from 1 day to 10 days. Subsequent storage of the cured units at 25° C. resulted in slower rates of loss of WS-12 to the LDPE (e.g., sorption) when compared to uncured units. After a curing period of 10 days at 40° C. (black circles), the content of WS-12 in the BFS units stored at 25° C. was constant over a period of 140 days.

Without being bound by theory, the curing technique described above may be saturating the BFS container walls with WS-12 such that no further loss occurs during long term storage at 25° C. The amount of WS-12 lost to the container walls during the curing period can be compensated for by adding an overage of WS-12 to the ophthalmic composition, such that the concentration of WS-12 after the curing period is 100% of the label claim. This strategy increases the feasibility of a physically stable pharmaceutical composition of WS-12 in a squeezable LDPE BFS container that can be stored at room temperature. This strategy can be applied to any type of LDPE regardless of the source of LDPE.

Storage under refrigerated conditions (e.g., at or below about 4° C.) may slow the sorption properties of the polyolefin container, but such storage conditions are not feasible under all conditions where an individual in need of the usefulness of the compositions provided herein resides. Accordingly, the compositions and processes provided herein address a need for shelf-stable storage of such useful compositions.

The present disclosure is not to be limited in scope by the specific embodiments describe herein. Indeed, various modifications of the disclosure in addition to those described herein will become apparent to those skilled in the art from the foregoing description and the accompanying figures. Such modifications are intended to fall within the scope of the appended claims.

What is claimed is:

1. A method of treating dry eye or reducing the likelihood of dry eye in a subject in need thereof, comprising administering to the subject a therapeutically effective amount of a liquid ophthalmic pharmaceutical composition, wherein the liquid ophthalmic pharmaceutical composition comprises a viscosity of less than 5 cP, and the liquid ophthalmic pharmaceutical composition comprises:
    about 0.003% w/v (1R,2S,5R)-2-isopropyl-N-(4-methoxyphenyl)-5-methylcyclohexane-1-carboxamide;
    about 0.14% w/v hypromellose;
    about 3.0% w/v polyoxyl 35 castor oil;
    about 0.78% w/v sodium dihydrogen phosphate dihydrate buffer;
    about 0.55% w/v NaCl;
    a pH of about 7; and
    water.

2. A method of treating an ophthalmic disease or disorder involving tear production or reducing the signs or symptoms of the ophthalmic disease or disorder in a subject in need thereof, comprising administering to the subject a therapeutically effective amount of a liquid ophthalmic pharmaceutical composition, wherein the liquid ophthalmic pharmaceutical composition comprises a viscosity of less than 5 cP, and the liquid ophthalmic pharmaceutical composition comprises:
    about 0.003% w/v (1R,2S,5R)-2-isopropyl-N-(4-methoxyphenyl)-5-methylcyclohexane-1-carboxamide;
    about 0.14% w/v hypromellose;
    about 3.0% w/v polyoxyl 35 castor oil;
    about 0.78% w/v sodium dihydrogen phosphate dihydrate buffer;
    about 0.55% w/v NaCl;
    a pH of about 7; and
    water.

3. A method of treating dry eye or reducing the likelihood of dry eye in a subject in need thereof, comprising administering to the subject a therapeutically effective amount of a liquid ophthalmic pharmaceutical composition, wherein the liquid ophthalmic pharmaceutical composition comprises a viscosity of less than 5 cP, and the liquid ophthalmic pharmaceutical composition comprises:
    about 0.0014% w/v (1R,2S,5R)-2-isopropyl-N-(4-methoxyphenyl)-5-methylcyclohexane-1-carboxamide;
    about 0.14% w/v hypromellose;
    about 3.0% w/v polyoxyl 35 castor oil;
    about 0.78% w/v sodium dihydrogen phosphate dihydrate buffer;
    about 0.55% w/v NaCl;
    a pH of about 7; and
    water.

4. A method of treating an ophthalmic disease or disorder involving tear production or reducing the signs or symptoms of the ophthalmic disease or disorder in a subject in need thereof, comprising administering to the subject a therapeutically effective amount of a liquid ophthalmic pharmaceutical composition, wherein the liquid ophthalmic pharmaceutical composition comprises a viscosity of less than 5 cP, and the liquid ophthalmic pharmaceutical composition comprises:
    about 0.0014% w/v (1R,2S,5R)-2-isopropyl-N-(4-methoxyphenyl)-5-methylcyclohexane-1-carboxamide;
    about 0.14% w/v hypromellose;
    about 3.0% w/v polyoxyl 35 castor oil;
    about 0.78% w/v sodium dihydrogen phosphate dihydrate buffer;
    about 0.55% w/v NaCl;
    a pH of about 7; and
    water.

* * * * *